US011324816B2

United States Patent
Galarza et al.

(10) Patent No.: US 11,324,816 B2
(45) Date of Patent: May 10, 2022

(54) HUMAN RESPIRATORY SYNCYTIAL VIRUS (HRSV) VIRUS-LIKE PARTICLES (VLPS) BASED VACCINE

(71) Applicant: TechnoVax, Inc., Elmsford, NY (US)

(72) Inventors: Jose M. Galarza, Elmsford, NY (US); Velasco Cimica, Elmsford, NY (US); Hélène Boigard, Chanceaux sur Choisille (FR)

(73) Assignee: TechnoVax, Inc., Elmsford, NY (US)

( * ) Notice: Subject to any disclaimer, the term of this patent is extended or adjusted under 35 U.S.C. 154(b) by 8 days.

(21) Appl. No.: 15/755,897

(22) PCT Filed: Aug. 29, 2016

(86) PCT No.: PCT/US2016/049226
§ 371 (c)(1),
(2) Date: Feb. 27, 2018

(87) PCT Pub. No.: WO2017/040387
PCT Pub. Date: Mar. 9, 2017

(65) Prior Publication Data
US 2019/0030156 A1    Jan. 31, 2019

Related U.S. Application Data

(60) Provisional application No. 62/212,306, filed on Aug. 31, 2015.

(51) Int. Cl.
*A61K 39/12*    (2006.01)

(52) U.S. Cl.
CPC .... *A61K 39/12* (2013.01); *C12N 2760/18323* (2013.01); *C12N 2760/18334* (2013.01); *C12N 2760/18523* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

| | | | |
|---|---|---|---|
| 7,704,720 B2 | 4/2010 | Tang | |
| 2008/0233150 A1* | 9/2008 | Smith | .......... A61K 39/155 424/211.1 |
| 2009/0220537 A1 | 9/2009 | Tindle et al. | |
| 2010/0040650 A1 | 2/2010 | Crowe, Jr. et al. | |
| 2011/0097358 A1 | 4/2011 | Galarza et al. | |
| 2014/0248314 A1 | 9/2014 | Swanson et al. | |
| 2015/0044248 A1 | 2/2015 | Schief | |

FOREIGN PATENT DOCUMENTS

| | | | |
|---|---|---|---|
| CN | 102858368 | 1/2013 | |
| CN | 104080476 | 10/2014 | |
| CN | 104293741 | 1/2015 | |
| WO | 2008148170 A1 | 12/2008 | |
| WO | 2010077712 | 7/2010 | |
| WO | WO-2011008974 A2 * | 1/2011 | .............. A61P 11/00 |

OTHER PUBLICATIONS

Cox et al., Journal of Virology p. 6368-6379 vol. 88 No. 11 (Year: 2014).*
McLellan et al. Science vol. 342, 592-598 (Year: 2013).*
McLellan et al.., Science: vol. 340, Issue 6136, pp. 1113-1117 (Year: 2013).*
Biacchesi et al., Journal of Virology vol. 80, Issue 12, pp. 5798-5806 (Year: 2006).*
Supplemental European Search Report for International Patent Application No. EP16842745.8 dated Jan. 30, 2019. 10 pages.
Cullen, Lori McGinnes, et al. "Murine immune responses to virus-like particle associated pre-and post-fusion forms of the respiratory syncytial virus F protein." Journal of virology (2015): JVI-00384.
Cimica, Velasco, et al. "A novel respiratory syncytial virus-like particle (VLP) vaccine composed of the postfusion and prefusion conformations of the F glycoprotein." Clinical and Vaccine Immunology (2016): CVI-00720.
International Preliminary Report on Patentability for International Patent Application No. PCT/US2016/049226 dated Mar. 15, 2018. 8 pages.
International Search Report and Written Opinion for International Patent Application No. PCT/US2016/049226 dated Feb. 23, 2017. 9 pages.
Chinese Patent Office Action dated Mar. 29, 2021 corresponding to Chinese Patent Application No. 201680064104.6; 15 pages.

* cited by examiner

*Primary Examiner* — Shanon A. Foley
*Assistant Examiner* — Myron G Hill
(74) *Attorney, Agent, or Firm* — Leason Ellis LLP

(57) ABSTRACT

Described herein are virus-like particles (VLPs) that display on their surfaces antigenic paramyxovirus (e.g., RSV and/or MPV) proteins. Also described are methods of making and using these VLPs.

16 Claims, 11 Drawing Sheets

Specification includes a Sequence Listing.

Fig.1D

[hRSV F]

[hMPV M]

[hRSV F] [hMPV M]

[hRSV F] [hMPV M]

Fig.1F

RSV Fusion — hMPV Matrix
| ED | TM | CT |—| M |
Peptide Linker

RSV Fusion — hMPV Matrix
| ED | TM |—| M |
Peptide Linker

ED: Extracellular Domain
TM: Transmenbrane Domain
CT: Cytoplasmic Tail

Postfusion F Construct

Prefusion F Constructs

Figure 2A
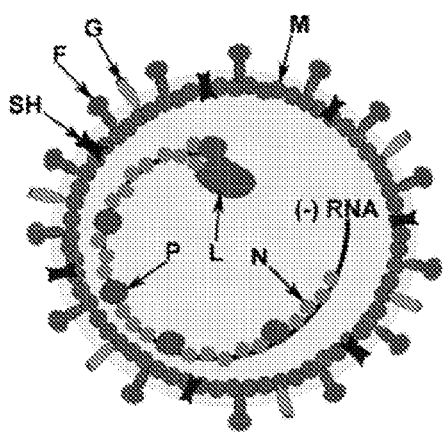
Figure 2B
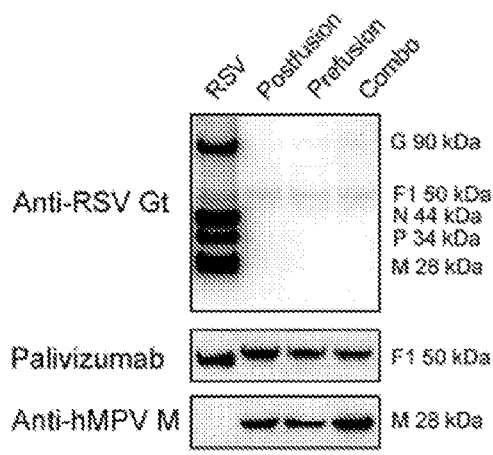
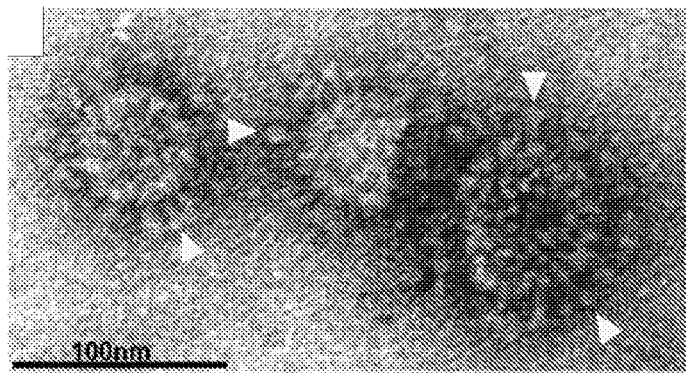
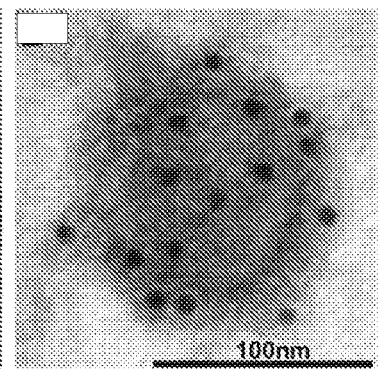
Figure 2C
Figure 2D Figure 4C                                               Figure 4D

Figure 6A
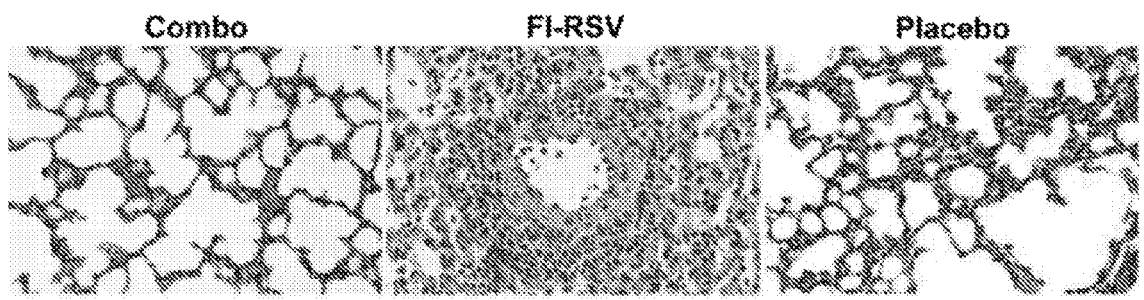
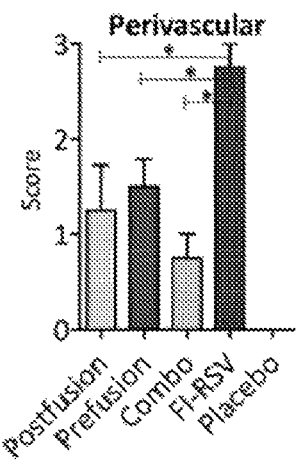
Figure 6B
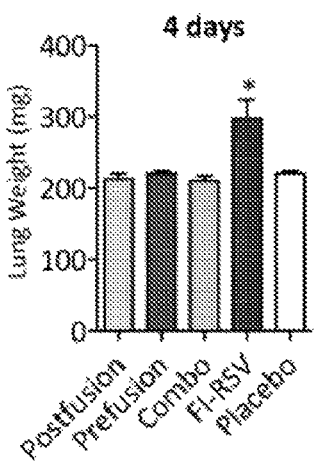
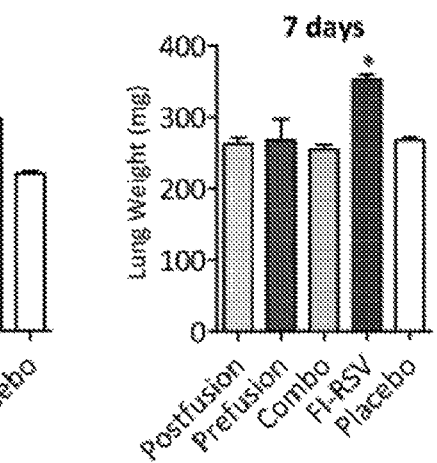
Figure 6C

Figure 7A

| F Constructs | Palivizumab | 5C4 |
|---|---|---|
| WildType | +++ | + |
| S155C-S290C (McLellan et al) | + | ++ |
| A102C-I148C | ++++ | ++ |
| N105C-G145C | ND | ND |
| N105C-I148C | ++++ | ++ |
| F32C-L467C | ND | ND |
| E30C-L467C | ND | ND |
| F32C-Y468C | ND | ND |
| F32C-V469C | ND | ND |
| A102C-I148C, S155C-S290C | +++ | ++++ |
| Furin Site 1* and Furin Site 2§ | +++ | ++ |
| Furin Site 1* and Furin Site 2§, A102C-I148C | +++ | +++ |
| Furin Site 1* and Furin Site 2§, A102C-I148C, S155C-S290C | ++ | ++++ |

\* Mutations Furin Site 1: R133K R135H R136Q

§ Mutations Furin Site 2: R106K R108H R109Q

- 1st Vaccination: VLPs, FI-RSV, PBS
- 2nd Vaccination: VLPs, FI-RSV, PBS
- RSV A Challenge $10^6$ pfu/animal Day 1 — 14 — 28 — 4 PC — 7 PC

- Pre-Immune Serum
- Immune Serum
- Serum, Lung
- Serum, Lung

Figure 7B

SEQUENCE LISTING

<160> NUMBER OF SEQ ID NOS: 8

<210> SEQ ID NO 1
<211> LENGTH: 574
<212> TYPE: PRT
<213> ORGANISM: Human respiratory syncytial virus

<400> SEQUENCE: 1

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
```

```
                       85                  90                  95
Met Gln Ser Thr Pro Ala Ala Asn Asn Arg Ala Arg Arg Glu Leu Pro
                    100                 105                 110

Arg Phe Met Asn Tyr Thr Leu Asn Asn Thr Lys Lys Thr Asn Val Thr
                    115                 120                 125

Leu Ser Lys Lys Arg Lys Arg Arg Phe Leu Gly Phe Leu Leu Gly Val
            130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                    165                 170                 175

Ala Val Val Ser Leu Ser Asn Gly Val Ser Val Leu Thr Ser Lys Val
                    180                 185                 190

Leu Asp Leu Lys Asn Tyr Ile Asp Lys Gln Leu Leu Pro Ile Val Asn
                    195                 200                 205

Lys Gln Ser Cys Arg Ile Ser Asn Ile Glu Thr Val Ile Glu Phe Gln
                    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                    245                 250                 255

Leu Leu Ser Leu Ile Asn Asp Met Pro Ile Thr Asn Asp Gln Lys Lys
                    260                 265                 270

Leu Met Ser Asn Asn Val Gln Ile Val Arg Gln Gln Ser Tyr Ser Ile
                    275                 280                 285

Met Ser Ile Ile Lys Glu Glu Val Leu Ala Tyr Val Val Gln Leu Pro
                    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                    325                 330                 335

Thr Asp Arg Gly Trp Tyr Cys Asp Asn Ala Gly Ser Val Ser Phe Phe
                    340                 345                 350

Pro Gln Ala Glu Thr Cys Lys Val Gln Ser Asn Arg Val Phe Cys Asp
                    355                 360                 365

Thr Met Asn Ser Leu Thr Leu Pro Ser Glu Val Asn Leu Cys Asn Val
                    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
                    420                 425                 430

Lys Thr Phe Ser Asn Gly Cys Asp Tyr Val Ser Asn Lys Gly Val Asp
                    435                 440                 445

Thr Val Ser Val Gly Asn Thr Leu Tyr Tyr Val Asn Lys Gln Glu Gly
                    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                    485                 490                 495

Glu Lys Ile Asn Gln Ser Leu Ala Phe Ile Arg Lys Ser Asp Glu Leu
                    500                 505                 510
```

```
Leu His His Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 2
<211> LENGTH: 539
<212> TYPE: PRT
<213> ORGANISM: Human metapneumovirus

<400> SEQUENCE: 2

Met Ser Trp Lys Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Glu Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Lys Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
```

```
            305                 310                 315                 320
Pro Asn Glu Lys Asp Cys Glu Thr Arg Gly Asp His Val Phe Cys Asp
                    325                 330                 335

Thr Ala Ala Gly Ile Asn Val Ala Glu Gln Ser Lys Glu Cys Asn Ile
                340                 345                 350

Asn Ile Ser Thr Thr Asn Tyr Pro Cys Lys Val Ser Thr Gly Arg His
            355                 360                 365

Pro Ile Ser Met Val Ala Leu Ser Pro Leu Gly Ala Leu Val Ala Cys
        370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
                420                 425                 430

Glu Gln His Val Ile Lys Gly Arg Pro Val Ser Ser Ser Phe Asp Pro
            435                 440                 445

Val Lys Phe Pro Glu Asp Gln Phe Asn Val Ala Leu Asp Gln Val Phe
        450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Gln Thr Gly Ala Pro Pro Glu Leu Ser
        515                 520                 525

Gly Val Thr Asn Asn Gly Phe Ile Pro His Ser
        530                 535

<210> SEQ ID NO 3
<211> LENGTH: 254
<212> TYPE: PRT
<213> ORGANISM: Human metapneumovirus

<400> SEQUENCE: 3

Met Glu Ser Tyr Leu Val Asp Thr Tyr Gln Gly Ile Pro Tyr Thr Ala
1               5                   10                  15

Ala Val Gln Val Asp Leu Val Glu Lys Asp Leu Leu Pro Ala Ser Leu
                20                  25                  30

Thr Ile Trp Phe Pro Leu Phe Gln Ala Asn Thr Pro Pro Ala Val Leu
            35                  40                  45

Leu Asp Gln Leu Lys Thr Leu Thr Ile Thr Thr Leu Tyr Ala Ala Ser
        50                  55                  60

Gln Ser Gly Pro Ile Leu Lys Val Asn Ala Ser Ala Gln Gly Ala Ala
65                  70                  75                  80

Met Ser Val Leu Pro Lys Lys Phe Glu Val Asn Ala Thr Val Ala Leu
                85                  90                  95

Asp Glu Tyr Ser Lys Leu Glu Phe Asp Lys Leu Thr Val Cys Glu Val
            100                 105                 110

Lys Thr Val Tyr Leu Thr Thr Met Lys Pro Tyr Gly Met Val Ser Lys
        115                 120                 125

Phe Val Ser Ser Ala Lys Pro Val Gly Lys Lys Thr His Asp Leu Ile
        130                 135                 140
```

```
Ala Leu Cys Asp Phe Met Asp Leu Glu Lys Asn Thr Pro Val Thr Ile
145                 150                 155                 160

Pro Ala Phe Ile Lys Ser Val Ser Ile Lys Glu Ser Glu Ser Ala Thr
                165                 170                 175

Val Glu Ala Ala Ile Ser Ser Glu Ala Asp Gln Ala Leu Thr Gln Ala
            180                 185                 190

Lys Ile Ala Pro Tyr Ala Gly Leu Ile Met Ile Met Thr Met Asn Asn
        195                 200                 205

Pro Lys Gly Ile Phe Lys Lys Leu Gly Ala Gly Thr Gln Val Ile Val
    210                 215                 220

Glu Leu Gly Ala Tyr Val Gln Ala Glu Ser Ile Ser Lys Ile Cys Lys
225                 230                 235                 240

Thr Trp Ser His Gln Gly Thr Arg Tyr Val Leu Lys Ser Arg
                245                 250

<210> SEQ ID NO 4
<211> LENGTH: 4
<212> TYPE: PRT
<213> ORGANISM: Human respiratory syncytial virus

<400> SEQUENCE: 4

Arg Ala Arg Arg
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Ala His Gln
1

<210> SEQ ID NO 6
<211> LENGTH: 4
<212> TYPE: PRT
<213> ORGANISM: Human respiratory syncytial virus

<400> SEQUENCE: 6

Arg Lys Arg Arg
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Lys Gln His
1

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Gly Gly Ser Gly Gly Ser Gly Gly Ser Gly Gly Ser Gly
1               5                   10
```

HUMAN RESPIRATORY SYNCYTIAL VIRUS (HRSV) VIRUS-LIKE PARTICLES (VLPS) BASED VACCINE

CROSS-REFERENCE TO RELATED PATENT APPLICATIONS

This application is a U.S. National Phase Application under 35 U.S.C. § 371 of International Patent Application No. PCT/US2016/049226, filed Aug. 29, 2016 and claims the benefit of priority under 35 U.S.C. Section 119(e) of U.S. Application Ser. No. 62/212,306, filed Aug. 31, 2015, all of which are incorporated by reference in their entireties. The International Application was published on Mar. 9, 2017 as International Publication No. WO 2017/040387 A2.

SEQUENCE LISTING

The instant application contains a Sequence Listing which has been submitted electronically in ASCII format and is hereby incorporated by reference in its entirety. Said ASCII copy, created on Feb. 27, 2018, is named 10050_006187-US1_SL.txt and is 13.1 bytes in size.

STATEMENT AS TO FEDERALLY SPONSORED RESEARCH

This work was supported in part by one or more grants from the National Institutes of Health (NIH). The U.S. Government may have certain rights in this invention.

TECHNICAL FIELD

The present invention is related to compositions comprising human Respiratory Syncytial Virus (hRSV) Virus-Like Particles (VLPs) and to methods of making and using these hRSV VLPs, including the creation and production of hRSV VLPs-based vaccines. In particular, the present disclosure includes strategies and methods used for the development of novel VLPs-based vaccine system able to protect humans against infection with different hRSV serotypes (A, and B). Also described herein are VLP production methods that produce VLPs that display certain optimized antigenic configurations and adjuvant formulation. These VLPs feature conformational epitopes relevant for the generation of an enhanced neutralizing immune response. VLPs vaccines can be produced in suspension cultures of eukaryotic cells following transient or stable transfection of protein expression vector/s. The VLPs are assembled at the cell membrane and released into the culture medium. After purification, concentration, and formulation the vaccine can be administered by a suitable route, for example, via either mucosal or parenteral routes, and induce an immune response able to protect against infection by the hRSV virus serotypes A and B.

BACKGROUND

Human Respiratory Syncytial Virus (RSV) is the leading cause of severe pediatric pulmonary disease worldwide. RSV infects nearly all infants at least once by the age of 2 years. The clinical spectrum of the RSV infection ranges from rhinitis in the upper respiratory tract, to pneumonia and bronchiolitis in the lower respiratory tract. Epidemiological studies around the globe indicate that 2-5% of the children infected with RSV require hospitalization with the most severe morbidity and mortality disproportionality affecting premature infants. RSV disease causes 100,000 to 200,000 fatalities annually. It is believed that severe RSV infection can predispose children to develop wheezing with future illnesses and potentially asthma. Importantly, RSV infection elicits neutralizing antibodies and a T-cell response that only lasts for a limited period of time; consequently the patient is often unprotected against reinfection. In addition, elderly people show a high risk of severe RSV disease upon reinfection with a significant morbidity and mortality. The CDC has reported that RSV infection is responsible for 177,000 hospitalizations and 14,000 deaths among adults over 65 annually in the United States.

Respiratory syncytial virus is an enveloped, single-stranded, negative-sense non-segmented RNA virus classified as a member of the Pneumovirus genus within the Paramyviridae family. The viral genome (15,522nt) encodes eleven proteins, eight structural (N, P, M, M2-1, SH, G, F, and L) and three non-structural (NS1, NS2, M2-2). The genome core is contained within the virus envelope which is underlined by M protein and decorated by three surface transmembrane glycoproteins G, F and SH. G is the major attachment protein while the F protein mediates membrane fusion and following replication syncytia formation. Antigenic dimorphism between the subgroups of RSV A and B is mainly linked to the G protein, whereas the F protein is more closely related between the subgroups. The G and F proteins contain the antigenic determinants that elicit the partially protective antibody response by the infected host. Antigenic variations on the G protein are the major determinants that differentiate the two RSV subtypes, A and B. Both of these subtypes circulate in humans, probably with similar incidence and virulence. The F and G proteins carry some CTL epitopes as well as the antigenic sites that elicit neutralizing antibodies. High titers of serum neutralizing antibodies prevent RSV infection of the lower respiratory tract, providing evidence for this as correlate of protection. Furthermore, the commercialized prophylactic MAb, Palivizumab, targets a neutralizing epitope in the highly conserved F proteins. These data provide the rationale for selecting these RSV surface antigens as targets to be incorporated onto the surface of the VLP vaccine. In addition, the F protein displayed on the surface of the virion rapidly changes conformation from a prefusion metastable form to a more stable postfusion configuration. Recent studies have shown that the prefusion conformation exhibit transient epitopes that are capable of eliciting antibodies with higher neutralizing power than those elicits by the postfusion structures. These data provides new insights for vaccine development. RSV VLPs are described, for example, in US Patent Publication Nos. 20080233150 and 20110097358.

Despite over 5 decades of research efforts, no licensed vaccine is currently available to control or prevent RSV infection. Indeed, RSV vaccine development has been hampered by the harmful outcome of the first clinical trials performed in the 1960s, which involved the use of the infamous formalin inactivated RSV vaccine (FI-RSV) Lot 100. The FI-RSV vaccine administered to children caused vaccine-enhanced disease after RSV natural infection and provoked an 80% rate of hospitalization and 2 deaths. Currently, the only pharmacological intervention available for RSV is immunoprophylaxis with a neutralizing monoclonal antibody directed to the RSV Fusion glycoprotein (F) Palivizumab (Synagis, MedImmune). Yet, Palivizumab prophylaxis is limited to only high-risk infants and its high cost is prohibitive for patients in developing countries.

Vaccinology research shows that the F glycoprotein is likely to be the most attractive target for eliciting neutralizing antibodies against the virus. The F protein shares a high degree of amino acid sequence conservation among different RSV isolates, it is localized on the surface of the virion, and it plays a pivotal role in the process of viral entry by triggering virion to target cell membrane fusion. Importantly, the F protein is also responsible for the typical histological manifestations of RSV infection in the lung epithelium including the formation of syncytia accompanied by cytopathic effects (CPE). Structural and genetic studies have shown that RSV F matures in the host and assembles as a membrane anchored homo-trimer. Furthermore, the RSV F protomer precursor (FO) is post-translationally activated in the Golgi apparatus by furin protease cleavages at sites I and II. The cleavage process generates two subunits, F1 and F2, joined together by two disulfide cysteine-cysteine bridges, and releases a short 27 amino-acid glycopeptide called p27. Thus, the N-terminus of the F1 subunit exposes the hydrophobic fusion peptide (FP), which triggers virion-cell fusion following its insertion in the target membrane. The C-terminus of RSV F1 contains the cytosolic tail (CT) domain that interacts with the matrix protein (M) during virion assembly.

RSV F is dynamically folded in different conformations that are antigenically distinct: the highly stable postfusion form, and the metastable prefusion form. Magro and colleagues (put ref at the patent end) (26) have demonstrated that prefusion F stimulates the production of antibodies with higher neutralizing activity in humans and rabbits than the postfusion conformation. Subsequently, McLellan and coworkers (25) determined by X-ray crystallography the protein structure of the prefusion F and identified the prefusion-only antigenic site φ, which is not present in the postfusion conformation of the F protein. While Palivizumab can recognize both postfusion and prefusion structures, a subset of highly neutralizing antibodies like 5C4, AM22 and D25 are able to interact specifically with the prefusion antigenic site φ. Interestingly, AM14 and MPE8 neutralizing antibodies are also able to very efficiently recognize the prefusion F using alternative antigenic sites. This demonstrates that the prefusion F expresses multiple epitopes suitable for target therapy, which are not exhibited in the postfusion conformation.

There is currently no licensed vaccine or specific treatment to control, combat or prevent hRSV infection. The prevention of infection by vaccination represents a critical unmet medical need of global significance. HRSV vaccines are being developed using conventional strategies. However, inactivated virus vaccine have triggered vaccine-enhanced disease in patients (13, 14, 15). Clinical trials with RSV live-attenuated vaccines candidates started in 1976. The experience with this approach has presented caveats in reaching a balance between vaccine attenuation and immunogenicity. Previous attempts with moderately attenuated vaccines were associated with relevant side effects such as nasal congestion, fever, pneumonia, cough and otitis media. On the other hand, vaccines with stronger level of viral attenuation were found to be inefficacious.

VLP vaccines as described herein are produced using recombinant expression of certain viral gene in eukaryotic cells. Licensed VLPs vaccines have been demonstrated to be efficacious, very safe and well tolerated for viral diseases such as hepatitis B virus (HBV), papilloma virus (HPV), hepatitis E virus (HEV). Previously tested subunit vaccines for hRSV were formulated using F in postfusion conformation. However, more recent studies have demonstrated that the F in prefusion conformation has the ability to elicit a superior level of neutralizing antibodies.

Our RSV VLP vaccines contain and display alternative conformations of the glycoprotein F (postfusion and prefusion) assembled using a matrix protein (M) of the human metapneumovirus (hMPV). This protein associates with the plasma membrane and forms a shell underlying the inner leaflet of the virion envelope in an analogous function to the RSV matrix. However, in the context of virus-like-particle morphogenesis, we have found that hMPV M protein drives the process of assembly and exit of VLP from the cell better than the homologous RSV M protein (data not shown). Several reports have shown that the role of the paramyxovirus F in particle formation depends on its cytoplasmic tail, which interacts with the M protein and facilitates the incorporation of F onto the surface of the viral particles. Consequently, we have replaced the cytoplasmic tail of the F protein with the analogous domain of the hMPV F protein in order to enhance recruitment of the RSV F to the budding site and concomitant incorporation onto the VLP surface.

In addition to its structural role, the hMPV M protein may enhance the immunogenicity of the VLP vaccine. hMPV M protein shares a high level of amino acid sequence homology with RSV M (63%), it can stimulate an innate immune response in vivo, and it has the ability to potentiate humoral and cellular immune responses. Testing of these VLP vaccines in animals subsequently infected with RSV showed that they induce a potent immune response, which suppress lung infection by the virus.

Therefore, new technologies are needed to develop safe and more effective hRSV vaccines.

SUMMARY

Described herein are virus-like particles (VLPs) comprising at least one antigenic RSV protein. Also described are compositions comprising these VLPs, as well as methods for making and using these VLPs. The VLPs described herein are devoid of viral genetic material and therefore unable to replicate or cause infection; however given their morphological, biochemical and antigenic similarities to wild type virions, VLPs are highly immunogenic and able to elicit robust protective immune responses. Unlike virion inactivated based vaccines, VLPs are not infectious eliminating the need for chemical treatment, thus maintaining the native conformation of components (structural and/or antigenic epitopes).

Thus, the invention describes a novel approach for RSV virus-like particle (VLP) development. In particular, we describe the creation, development and production of VLP vaccines for RSV that will trigger, upon human immunization, a strong and balanced immune response characterized by the induction of high level of neutralizing antibodies again hRSV A and/or B serotypes, including both A and B serotypes concurrently.

Based on paramyxovirus subviral particles studies as well as on our own experience in VLPs assembly, we have designed a new and effective strategy for the formation and release of hRSV VLPs. We have discovered that the co-expression of the recombinant engineered Fusion Glycoprotein (F) and Matrix protein (M) from human Metapnuemovirus (hMPV) triggers assembly and production of RSV VLPs, which VLPs elicit immune responses when administered to subjects, including induction of neutralizing antibodies. In certain embodiments, the VLPs display (e.g., on their surface), RSV F protein(s) that exhibit different reactivities (e.g., as demonstrated by monoclonal antibodies that recognize structural features of the F protein). Display on the VLPs as described herein of different F protein conformations seem to be highly relevant for the elicitation of potent neutralizing antibody in humans.

In one aspect of the invention, described herein are paramyxovirus (hRSV and/or hMPV) virus-like particles (VLPs) (also known as subviral particles, recombinant subviral particles, biological nanoparticles, nanoparticles, etc.) utilizing structural F and M recombinant viral proteins from hRSV and/or hMPV. These VLPs can be used as vaccine or immunogens for protecting against infection with paramyxoviruses, including hRSV serotypes A and B.

Thus, described herein is a virus-like particle (VLP) comprising at least one metapneumovirus (MPV) protein (e.g., human MPV (hMPV) matrix (M) protein); and at least one MPV or respiratory syncytial virus (RSV) protein (e.g., one or more F proteins, one or more G proteins and/or one or more SH proteins). The proteins may be wild-type or modified, including, but not limited to, codon optimized proteins, proteins with modifications at one or more amino acids (mutations, deletions, insertions) and/or hybrid (chimeric) proteins including sequences from different pneumoviruses in one protein (e.g., a protein in which the transmembrane and/or cytoplasmic domains of the F protein (e.g., RSV) are replaced with amino acid sequences from a different pneumovirus F protein (e.g., MPV)). In certain embodiments, the modifications comprise a substitution at one or more of residues 30, 32, 102, 105, 145, 148, 155, 290, 467, 468, 106 to 109 and/or 133 to 136, numbered relative to SEQ ID NO:1 (e.g., substitution of a cysteine (C) residue for the wild-type residue). In any of the VLPs described herein, the one or more F proteins may comprise prefusion F protein configurations and/or postfusion F protein configurations.

Also provided herein is DNA construct comprising sequences encoding pneumovirus viral proteins used to assemble one or more of the VLPs described herein, the DNA construct comprising sequences encoding the proteins of the VLP. A method of producing a VLP comprising introducing into a host cell (e.g., a eukaryotic cell selected from the group consisting of mammalian, yeast, insect, plant, amphibian and avian cells) one or more DNA constructs described herein under conditions such that the cell produces the VLP is also provided (e.g., the cells are cultured at temperatures ranging from 25° C. to 37° C.). VLP(s) generated by any of the methods described herein are also provided.

Also provided is an immunogenic composition comprising at least one VLP as described herein. The immunogenic compositions as described herein may further include an adjuvant.

In a still further aspect, provided herein is a method of generating an immune response to one or more pneumoviruses in a subject (e.g., human), the method comprising administering to the subject an effective amount of one or more immunogenic compositions as described herein. The immunogenic compositions may be administered mucosally, intradermally, subcutaneously, intramuscularly and/or orally. In certain aspects, the immune response vaccinates the subject against multiple serotypes or clades of one or more pneumoviruses.

In another aspect, methods of generating (assembling) the paramyxovirus (e.g., hRSV) VLPs described herein are provided. In certain embodiments, such methods and strategies involve mutations, deletions, and insertions of the gene used to produce VLPs. In other embodiments, expression conditions that enhance particle stability, morphogenesis and egress from producing cells are employed. (e. g. supplements and conditions: sodium orthovanadate, sodium pyruvate, valproic acid, sorbitol, caffeine, L-glutamine, amino acids, non-essential amino acid, ITSE (insulin-Transferrin-Selenium-Ethanolamine), lipid supplements, sucrose or glucose, growth factors, concentration of $CO_2$, etc.

Also described are strategies for the assembly of VLPs displaying on its surface the F protein of a single conformation (postfusion or prefusion), or the combination of the postfusion and prefusion conformations in the VLPs. In certain embodiments, combining VLPs with alternative antigenic sites present in both postfusion and prefusion conformations allows for the formulation of optimized vaccine able to elicit higher immune protection and preventing development of viral mutants that could evade the immune system. Furthermore, production of VLPs can be attained in suspension culture of eukaryotic cells following the expression of the selected genetically modified recombinant protein F and M (e.g., RSV or MPV F proteins and MPV M proteins). Both transient and stable transfection methods can be used to introduce into cells the plasmids that direct proteins expression. VLPs are released from the producing cells into the culture medium from where they are collected and purified by different biochemical methods such as gradient centrifugation, filtration and chromatography or combination thereof.

In yet another aspect, described herein is the formation of VLPs containing paramyxovirus (e.g., RSV or MPV) F protein(s) of different structural conformation resulting from amino-acidic sequence modification developed using structural vaccinology and molecular biology techniques. These VLPs show differential reactivity with a specific monoclonal antibody that recognizes the F protein, reflecting their conformational differences. In addition, VLPs produced with F proteins in different conformation are able to induce stronger titers of neutralizing antibodies when administered as vaccine to small animal models. The utility of the paramyxovirus VLPs may include, but it is not limited to, vaccine and immunological use, as adjuvant, and/or immune-modulators, delivery vehicle for heterologous proteins or small molecules as well as prophylactic and therapeutic applications.

Different reports have shown that the role of paramyxovirus F protein in particle formation depends on its cytoplasmic tail that is required for interactions with M and incorporation of F inside the viral particles. In yet another aspect, described herein is the modification of hRSV F constructs for expression of hybrid protein with substitution of cytoplasmic tail from hMPV F. The modification allows for the interaction of hRSV F with hMPV M and formation of VLPs including the alternative structures of the F protein.

Also provided are VLPs produced by any of the methods described herein.

Thus, the invention includes but is not limited to the following embodiments:
1. A paramyxovirus Virus-Like Particles (VLP) comprising the proteins F from human Respiratory Syncytial Virus (hRSV), wherein said paramyxovirus is for hRSV.
2. A paramyxovirus Virus-Like Particle (VLP) comprising the proteins F from human RSV (hRSV) and M from human Metapneumovirus (hMPV) that are assembled following the co-expression, wherein said paramyxovirus is for hRSV.
3. A hRSV virus-like particle of 2 and wherein the proteins are produced from separate transcription units for hRSV F and hMPV M.
4. A DNA construct comprising an optimized and/or modified sequences encoding hRSV F protein (Gen- Bank: AC083302.1, SEQ ID NO:1) used to assemble VLPs and including amino-acids modification for inducing prefusion conformation.

5. The DNA construct hRSV F from 4 with following amino-acids substitutions for creating disulfide bridges between F2-F1 subunits: A102C and I148C, or N105C and G145C, or A102C and G145C, or N105C and I148C, or E30C and L467C, or E30C and Y468C, or E30C and V469C, or F32C and L467C, or F32C and Y468C, or F32C and V469C.
6. The DNA construct of 4 with Furin Site I mutations (R133K, and R135Q, and R136H) and or Furin Site I1 mutations (R106K, and R108H, and R109Q).
7. The DNA construct 4 with any possible combination of amino-acids substitution described in 5 plus the amino-acids substitution S155C and S290C: e.g. A102C and I148C plus S155C and S290C.
8. The DNA construct 4 with any combination of amino-acid substitution described in 5 plus the amino-acids substitution described in 6: Furin Site I mutation (R133K, and R135Q, and R136H), or/and Furin Site II mutations (R106K, and R108H, and R109Q). For an example: A102C, and I148C, plus R133K, and R135H, and R136Q, plus R106K, and R108H, and R109Q.
9. The DNA construct 4 with any combination of amino-acid substitution described in 5, plus the amino-acids substitution described in 6, plus the amino-acids substitution S155C and S290C.
10. The DNA constructs 4 to 9 with cytoplasmic tail (CT) and transmembrane domain (TD) amino-acids sequences exchanged with the CT and TD from hMPV F: hRSV F truncated sequence from amino-acid 1-524 joined with hMPV F truncated sequence from amino-acid 489-539 (GenBank: AEK26895.1, SEQ ID NO:2). The DNA constructs 4 to 9 where only the CT or TM amino-acids sequences exchanged with the equivalent sequences of hMPV F. Such modifications allow an improved formation of VLPs containing recombinant proteins hRSV F and hMPV M.
11. The DNA constructs 4 to 10 joined with a sequence coding a peptide linker and hMPV M protein (FIG. 1F).
12. DNA constructs 4 to 10 with cytoplasmic tail (CT) truncation joined with a peptide linker and hMPV M protein (FIG. 1F).
13. A method of producing VLPs comprising selected gene products, the method comprising transiently transfecting a eukaryotic cell one or more plasmids comprising sequences encoding the selected gene products such that the VLPs are produced by the eukaryotic cell. The expression conditions are altered to favor the retention of labile epitopes.
14. A method of producing VLPs comprising selected gene products, the method comprising stably integrating one or more sequences encoding the selected gene products into the genome of a eukaryotic cell such that the eukaryotic cell produces the VLPs.
15. The method of 11 or 12, wherein said eukaryotic cell is selected from the group consisting of mammalian, yeast, insect, plant, amphibian and avian cells.
16. A VLPs generated by the method of any of 11-13.
17. A vaccine VLPs-based formulated with only hRSV postfusion F, with or without hMPV M.
18. A vaccine VLPs-based formulated with hRSV prefusion F, with or without hMPV M.
19. A vaccine VLPs-based formulated with combination of hRSV postfusion and prefusion F with or without hMPV M.
20. VLPs vaccines 15-17 formulated with an adjuvant.

These and other embodiments will be readily apparent in light of the instant disclosure.

BRIEF DESCRIPTION OF THE DRAWINGS

FIG. 1A is a schematic representation of wild type (WT) RSV F primary structure (top panel). The RSV F protein matures by furin enzyme cleavage at sites I and II generating F2-F1 protomer and releasing p27 glycopeptide. The RSV F protein is characterized by heptad repeat domains HRA, HRB and HRC, fusion peptide (FP), transmembrane domain (TM) and cytosolic tail (CT), which is important for virion assembly with the matrix M protein. The F protein elicits neutralizing antibodies able to recognize the antigenic sites: φ, I, II, and IV. Also shown are schematics of postfusion hybrid construct ("Post") (middle panel) with swapped CT and TM with the analogous domain of the hMPV-F (right most shaded bar under "hMPV" in middle and bottom panels) and of a prefusion hybrid construct ("Pre") (bottom panel) with amino acid (disulfide bond) modifications at one or more of residues between 102-148 and 155-290. FIG. 1B is a tridimensional structure representation of F protomer in postfusion and prefusion conformation. The cysteine modifications A102C and I148C are indicated by the shaded ovals. Prefusion conformation is triggered by formation of cysteine link between F2 and F1 chains. FIG. 1C is a graph showing results of a dot blot analysis demonstrating the immune reactivity of recombinant F proteins. The graph represents the results of 3 independent experiments for 5C4, a mouse monoclonal antibody (mAb) specific for the prefusion-only antigen site Φ (Note: this is the Greek letter Phi), normalized over Palivizumab immune-reactivity: the asterisk indicates a statistically significant p-value ($p<0.05$) between the postfusion and prefusion conditions; ND stands for not detected. Included below is a figure of a single dot blot experiment. FIG. 1D depicts human Respiratory Syncytial Virus (hRSV) Fusion protein (F) and human Metapneumovirus Matrix protein (M) genes selected for Virus-Like Particles (VLPs) assembly and their different configurations in expression vectors. FIG. 1E the different modification of hRSV F for inducing prefusion conformation. FIG. 1F illustrates hRSV F linked with hMPV M. FIG. 1G shows the antigenic composition of single VLP and options for formulating combination of vaccines with different conformation of hRSV F.

FIGS. 2A through 2D depicts structure and morphology of RSV VLPs using recombinant RSV F and hMPV M. FIG. 2A is a schematic drawing of RSV viral particle: F, G, SH, M, P, N, and L proteins, and genomic negative RNA are indicated. FIG. 2B depicts result of Western blot analysis of RSV VLPs using different antibodies such as Anti-RSV from goat (Anti-RSV Gt), Palivizumab, and anti-hMPV M. FIG. 2C shows purified RSV VLPs were negatively stained and examined by electron microscopy. The micrograph shows spherical and irregular particles (90-100 nm) decorated with surface projections or "spikes" (arrowheads) resembling the morphology of RSV virion. FIG. 2D shows electron micrographs of immunogold-labeled RSV VLPs probed with the humanized monoclonal antibody Palivizumab and developed with a goat anti-human antibody coupled to gold spheres (10 nm). Detection of gold spheres demonstrates that F is decorating the surface of the VLPs.

FIG. 3A is a graph showing plaque assay analysis of viral titers in the mouse lungs 4 days post-challenge shows undetectable viral replication in VLP vaccinated mice, whereas the placebo control group demonstrates a very productive infection; dotted line indicates the lower detection limit. FIG. 3B is a graph showing viral micro-neutralization assay and shows the level of serum neutralizing antibody after vaccination. VLP combo vaccination resulted in a statistically significant enhancement of neutralizing antibody with respect to VLP prefusion and postfusion vaccination ($p<0.05$). FIG. 3C is a graph showing measurement of serum antibodies after immunization prior viral challenge at the indicated conditions. FIG. 3D Analysis of the ratio between IgG2a and IgG1 demonstrates that VLP combo vaccine induces a superior Th1-mediated response. The results in FIGS. 3A through 3D were generated using 4 mice per each condition.

FIGS. 4A through 4D are graphs showing cytokine responses at the indicated conditions in VLPs vaccinated mice lung after RSV infection. FIG. 4A shows cytokines for Th1-mediated response are: IFNγ (left graph), IL-12p40 (middle graph), and TNFα (right graph). FIG. 4B shows Th2-mediated response cytokine measurement includes IL-4 (left graph), IL-5 (middle graph), and IL-13 (left graph). FIG. 4C shows IL-17 (left graph) and IL1-β (right graph) analysis indicates Th17-mediated response. FIG. 4D shows IL-10 cytokine levels and demonstrates immune-regulatory process development. Results were generated using a group of 4 mice per each condition 4 days post-infection. The asterisk indicates statistically significant differences between the experimental condition and the placebo control, "ND" indicates not detectable.

FIGS. 6A through 6C show RSV VLP vaccines do not induce "vaccine-enhanced disease" in murine lung. FIG. 6A shows hematoxylin and eosin staining of mouse lung 4 days after viral challenge: Microscopic examination of lungs from combo vaccination (left panel) shows absence or minor pulmonary pathology. On the other hand, the FI-RSV vaccination induces a very high perivascular immune infiltration (middle panel). A placebo control is included as a reference (right panel). FIG. 6B is a graph showing perivascular infiltration as scored by blind evaluation of hematoxylin and eosin stained sections of mouse lung 4 days after viral challenge, the score ranges from 0 for normal to maximum of 3 for massive infiltration, the asterisk indicates a statistically significant difference between VLP vaccination versus FI-RSV. FIG. 6C shows graphs of mouse lung was harvested 4 days (left panel) and 7 days (right panel) post RSV-challenge and weighed; the asterisk indicates statistically significant difference with respect to the placebo control ($p<0.05$).

FIGS. 7A through 7C show immunization of mice with compositions as described herein. FIG. 7A is a Table showing a list of prefusion F constructs generated by mutagenesis and analyzed by ELISA using different antibodies against F protein: prefusion antibody 5C4, postfusion antibody 131-2A, and anti-F antibody Palivizumab (Synagis, MedImmune). FIG. 7B shows a diagram of the Vaccination schedule used in BALB/C mice seronegative mice were immunized by intramuscular injection at day 1 and 14. Mice were challenged with $1\times10^6$ pfu of RSV A Long strain administered via the intranasal route at day 28; animals were sacrificed at days 4 and 7 post RSV-challenge (PC). FIG. 7C is a graph showing mouse body weight measurements after immunization and viral challenge. Mice were immunized and infected following the protocol described in FIG. 7B and the Materials and Methods section. Results shown were generated from data of 10 mice per condition.

DETAILED DESCRIPTION

Figure 1:
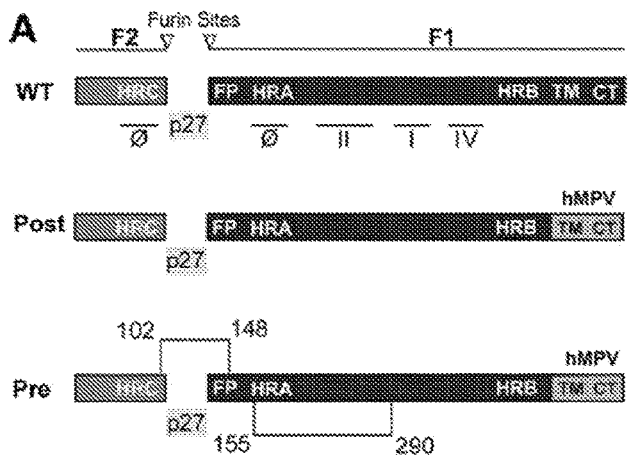
FIGS. 1A through 1G depict structural development of RSV F constructs using structural vaccinology.
Figure 1:
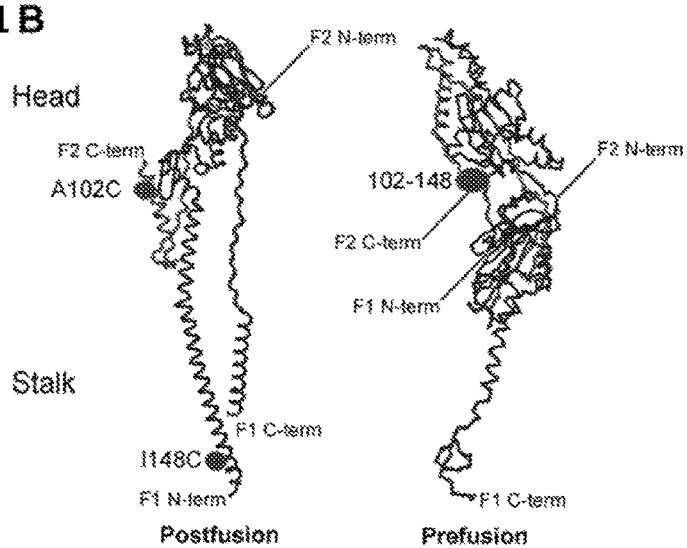
Figure 1:
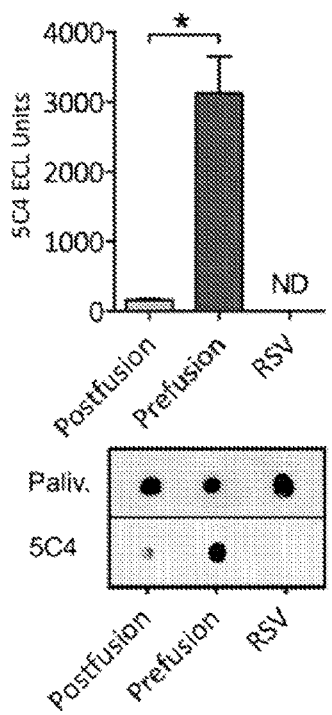
Figure 1E:
Figure 1E:
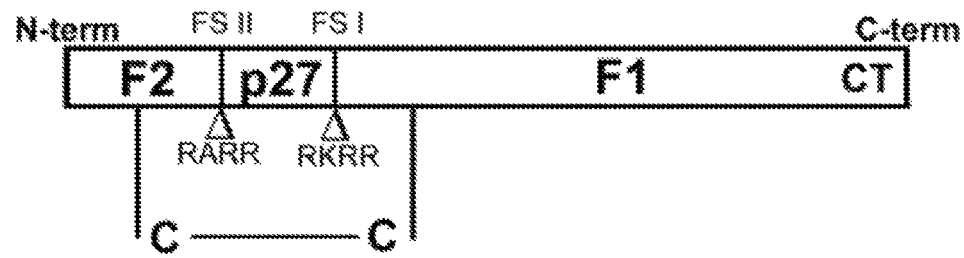
Figure 1E:
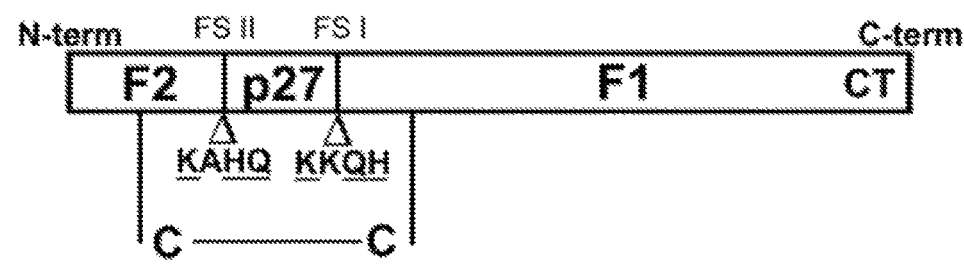
Figure 1E:
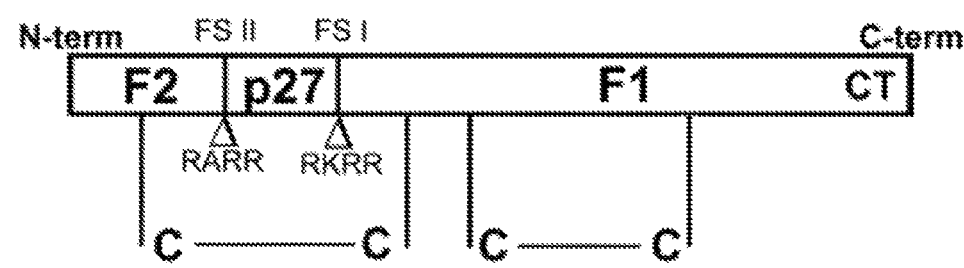
Figure 1E:
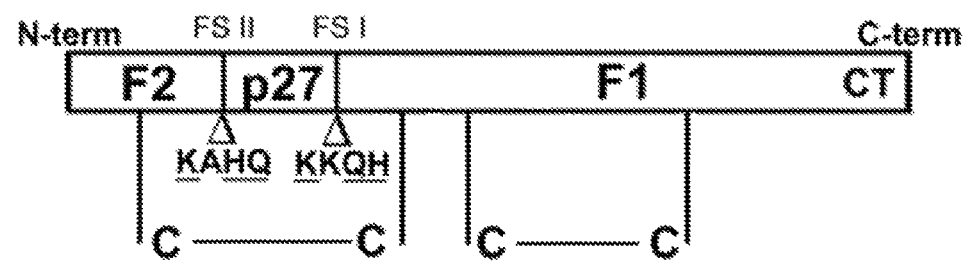
Figure 1G:
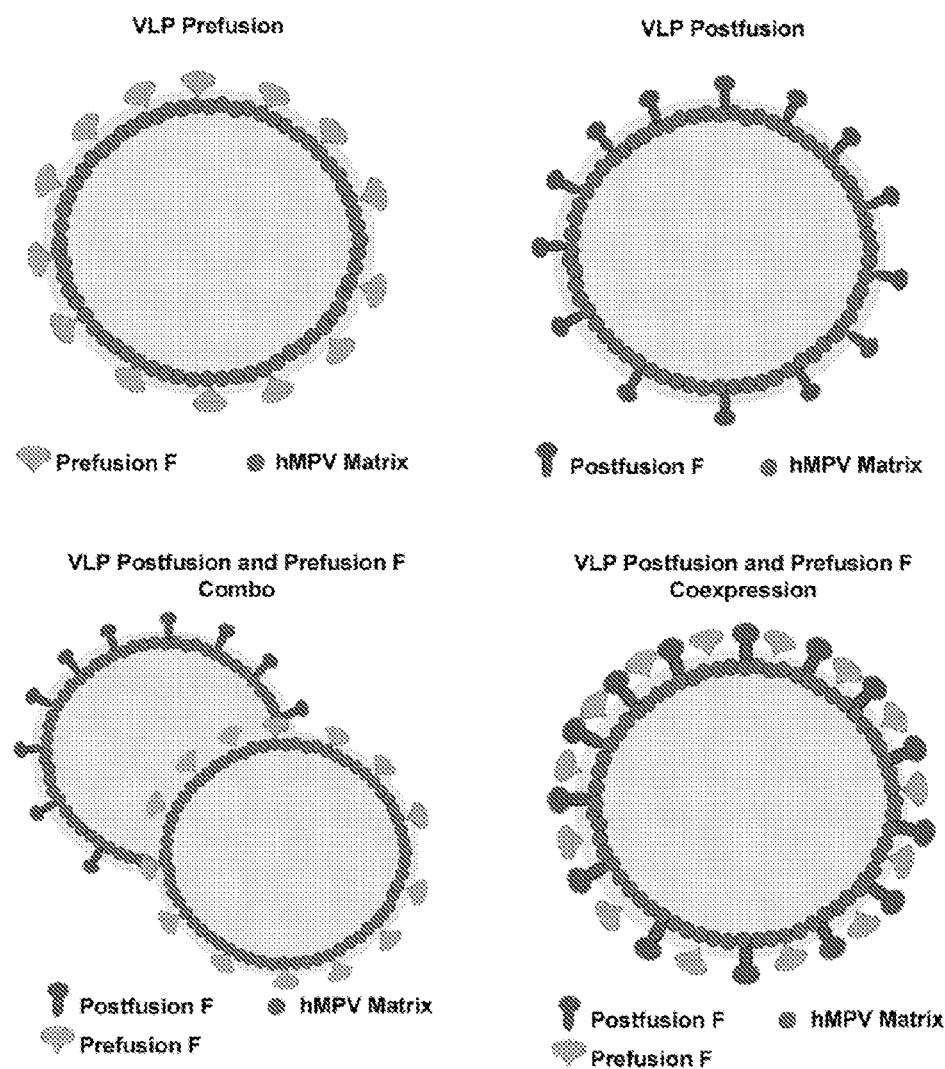

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Short Protocols in Molecular Biology, 4th ed. (Ausubel et al. eds., 1999, John Wiley & Sons); Molecular Biology Techniques: An Intensive Laboratory Course, (Ream et al., eds., 1998, Academic Press); PCR (Introduction to Biotechniques Series), 2nd ed. (Newton & Graham eds., 1997, Springer Verlag); Fundamental Virology, Second Edition (Fields & Knipe eds., 1991, Raven Press, New York).

All publications, patents and patent applications cited herein are hereby incorporated by reference in their entirety.

As used in this specification and the appended claims, the singular forms "a," "an" and "the" include plural references unless the content clearly dictates otherwise. Thus, for example, reference to "a VLP" includes a mixture of two or more such VLPs.

Definitions

As used herein, the terms "sub-viral particle" "virus-like particle", "recombinant subviral particles" or "VLP" refer to a nonreplicating, viral shell. VLPs are generally composed of one or more viral proteins, such as, but not limited to those proteins referred to as capsid, coat, shell, surface and/or envelope proteins, or particle-forming polypeptides derived from these proteins. VLPs can also be described as "enveloped" if they contain a cell derived lipid membrane as the RSV and hMPV described here or non-enveloped if assembly with protein without a lipid membrane. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical and immunological characterizations, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions. Additional methods of VLP purification include but are not limited to chromatographic techniques such as affinity, ion exchange, size exclusion, and reverse phase procedures.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those, which are conservative in nature, i.e., those substitutions that take place within a family of amino acids that are related in their side chains. Specifically, amino acids are generally divided into four families: (1) acidic-aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a cytotoxic T lymphocyte (CTL) epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term includes polypeptides which include modifications, such as deletions, additions and substitutions (generally conservative in nature) as compared to a native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytotoxic T lymphocytes ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences, and/or sequence elements controlling an open chromatin structure see e.g., McCaughan et al. (1995) PNAS USA 92:5431-5435; Kochetov et al (1998) FEBS Letts. 440:351-355.

A "nucleic acid" molecule can include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when active. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable programs for calculating the percent identity or similarity between sequences are generally known in the art.

A "vector" is capable of transferring gene sequences to target cells (e.g., bacterial plasmid vectors, viral vectors, non-viral vectors, particulate carriers, and liposomes). Typically, "vector construct," "expression vector," and "gene transfer vector," mean any nucleic acid construct capable of directing the expression of one or more sequences of interest in a host cell. Thus, the term includes cloning and expression vehicles, as well as viral vectors. The term is used interchangeable with the terms "nucleic acid expression vector" and "expression cassette."

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any unacceptable biological effects or interacting in a deleterious manner with any of the components of the composition in which it is contained.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

As used herein the term "adjuvant" refers to a compound that, when used in combination with a specific immunogen (e.g. a VLP) in a formulation, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses.

As used herein an "effective dose" generally refers to that amount of VLPs of the invention sufficient to induce immunity, to prevent and/or ameliorate an infection or to reduce at least one symptom of an infection and/or to enhance the efficacy of another dose of a VLP. An effective dose may refer to the amount of VLPs sufficient to delay or minimize the onset of an infection. An effective dose may also refer to the amount of VLPs that provides a therapeutic benefit in the treatment or management of an infection. Further, an effective dose is the amount with respect to VLPs of the invention alone, or in combination with other therapies, that provides a therapeutic benefit in the treatment or management of an infection. An effective dose may also be the amount sufficient to enhance a subject's (e.g., a human's) own immune response against a subsequent exposure to an infectious agent. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease and/or reduces the severity of symptoms.

As used herein, the term "effective amount" refers to an amount of VLPs necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to VLPs of the invention. The term is also synonymous with "sufficient amount."

As used herein, the term "multivalent" refers to VLPs which have multiple antigenic proteins against multiple types or strains of infectious agents or alternative conformations of the same antigen/protein (metastable), which naturally transition from one conformation to the next, but in the context of a vaccine formulation may contain stabilized (fixed) form of one conformation or both.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interferons, interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as VLPs of the invention, or can be administered separately. Either the protein or an expression vector encoding the protein can be administered to produce an immunostimulatory effect.

As used herein the term "protective immune response" or "protective response" refers to an immune response mediated by antibodies against an infectious agent, which is exhibited by a vertebrate (e.g., a human), that prevents or ameliorates an infection or reduces at least one symptom thereof. VLPs of the invention can stimulate the production of antibodies that, for example, neutralize infectious agents, blocks infectious agents from entering cells, blocks replication of said infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates pneumovirus (e.g., RSV) infection or reduces at least one symptom thereof.

As use herein, the term "antigenic formulation" or "antigenic composition" refers to a preparation which, when administered to a vertebrate, e.g. a mammal, will induce an immune response.

As used herein, the term "vaccine" refers to a formulation which contains VLPs of the present invention, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

General Overview

This invention describes the formation of biological particles (e.g., VLPs) that mimic the structure in size, morphology and biochemical composition of a pneumovirus; however, they are devoid of a fully competent viral genome and therefore unable to cause infection or disease. The lack of viral genome and lack of infectivity of the pneumovirus (e.g., RSV and/or MPV) VLPs eliminate the need of chemical inactivation better preserving therefore their structures, protein conformations and antigenic properties enhancing immunogenicity and potency as vaccine. These biological mimics are identified as virus-like particles (VLPs). VLPs are assembled using genetic information comprising segments of the virus genome encoding selected proteins that may include but not limited to structural and/or non-structural protein or combination of proteins with analogous functions derived from close related viruses (e.g. RSV and hMPV). The viral sequences in DNA form can be organized in a single transcription unit (segment) that expresses a single polypeptide or in separate transcription units (segments) each one expressing a single protein.

Virus-Like Particles

The present disclosure relates to paramyxovirus VLPs, which VLPs carry on their surfaces one or more modified antigenic pneumovirus proteins. This VLP, alone or in combination with one or more additional VLPs and/or adjuvants, stimulates an immune response that protects against pneumovirus (e.g., RSV) infection.

This invention describes the formation of biological particles that mimic the structure in size, morphology and biochemical composition of native human Respiratory Syncytial Virus (hRSV) and paramyxovirus and are thus able to elicit strong immune responses. However, they are devoid of a fully competent viral genome and therefore unable to cause infection or disease. These biological mimics are identified as virus-like particles (VLPs). VLPs are assembled using genetic information comprising segments of the hRSV genome encoding F proteins that may include but not limited to human Metapneumovirus (hMPV) Matrix (M) and other proteins from paramyxovirus. As shown in FIG. 1, the viral sequences in DNA form can be organized transcription units (segment) in separate expression vectors each expressing a single polypeptide or in a single vector that is able to express simultaneously multiple transcription units.

The proteins used in the VLPs described herein may be wild-type or modified. Modifications include, but are not limited to, substitutions, deletions and/or insertions as well as codon optimization.

In certain embodiments, the VLPs comprise an RSV F protein displayed on the surface of a VLP made with one or more structural proteins (e.g., hMPV matrix protein), where the one or more structural proteins form a scaffold (e.g., circular) from which the antigenic (e.g., F proteins) are displayed.

An exemplary wild-type F protein (RSV) is shown below (SEQ ID NO:1). Furin cleavage sites are bolded and residues that may be targeted for modification (e.g., substitution) are underlined. The cytoplasmic tail/transmembrane domain that may be replaced with analogs sequences from other viruses (e.g., hMPV F protein) are shown in italics.

Wild type RSV F (SEQ ID NO: 1):
MELPILKANAITTILAAVTFCFASSQNITE<u>EF</u>YQSTCSAVSKGYLSALRT

GWYTSVITIELSNIKENKCNGTDAKVKLIKQELDKYKNAVTELQLLMQST

P<u>A</u>ANNRARRELPRFMNYTLNNTKKTNVTLSKKRKRRFLGFLLGV<u>GSAI</u>AS

GIAVSKVLHLEGEVNKIKSALLSTNKAVVSLSNGVSVLTSKVLDLKNYID

KQLLPIVNKQSCRISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKS<u>LYV</u>KGEPIINFYDPLVEPSDEFDASISQVNEKIN

QSLAFIRKSDELLHHVNAGKSTTN*IMITTIIIVIIVILLSLIAVGLLLYC*

*KARSTPVTLSKDQLSGINNIAFSN*

The F protein(s) is used herein may include one or more modifications. In certain embodiments, the F protein is codon optimized and/or includes one or more amino acid modifications, as numbered relative to SEQ ID NO:1. Residues that may be subject to modification are underlined above, for example, substitutions to create cysteines for disulfide bonds at one or more of residue 30 (e.g., E30C), residue 32 (e.g., F32C), residue 102 (e.g., A102C), residue 105 (e.g., N105C), residue 145 (e.g., G145C), residue 148 (e.g., I148C) residue 155 (e.g., S155C), residue 290 (e.g., S290C), residue 467 (e.g., L467C), residue 468 (Y486C), residue 469 (V469C) and combinations thereof (e.g., S155C-S290C1; A102C-I148C; N105C-G145C; N105C-I148C, E30C-L467C, F32C-Y468C, F32C-V469C). Two or more different mutations or combinations may also be used (e.g., A102C-I148C with S155C-S290C). In addition, a single VLP can include different F proteins (e.g., RSV and/or MPV, hybrids), etc. Similarly, multiple VLPs with one or multiple different F proteins can be combined for use as described herein.

In any of the embodiments described herein, the paramyxovirus F protein may include modifications to one or more of the furin cleavage sites, numbered relative to SEQ ID NO:1. In certain embodiments, the furin cleavage site RARR (SEQ ID NO: 4; residues 106 to 109 of SEQ ID NO:1, bolded above) are modified to KAHQ (SEQ ID NO: 5). In other embodiments, the furin cleavage site RKRR (SEQ ID NO: 6; residues 133 to 136 of SEQ ID NO:1, bolded above) are modified to KKQH (SEQ ID NO: 7). In other embodiments, both furin cleavage sites are modified.

In additional embodiments, the paramyxovirus F protein (s) used to make the VLPs described herein comprise a chimera (hybrid) of RSV sequences (modified or wild-type) with additional sequences from other viruses, for example from other pneumoviruses. By way of non-limiting example, the constructs used to generate RSV F proteins can include hMPV sequences, for example at in the transmembrane and/or cytoplasmic tail (CT) regions (see, FIG. 1A).

An exemplary hMPV F protein sequence is shown in GenBank AEK26895.1 below (SEQ ID NO:2), in which the cytoplasmic tail and transmembrane regions (489-539) are underlined:

Wild-type hMPV F protein (SEQ ID NO: 2):
MSWKVVIIFSLLITPQHGLKESYLEESCSTITEGYLSVDRTGWYTNVFTL

EVGDVENLICADGPSLIKTELELTKSALRELKTVSADQLAREEQIENPRQ

SRFVLGAIALGVATAAAVTAGVAIAKTIRLESEVTAIKNALKKTNEAVST

LGNGVRVLATAVRELKDFVSKNLTRAINKNKCDIDDLEMAVSFSQFNERF

LNVVRQFSDNAGITFAISLDLMTDAELARAVSNMPTSAGQIKLMLENRAM

VERKGFGILIGVYGSSVIYMVQLPIFGVIDTPCWIVKAAPSCSKKKGNYA

CLLREDQGWYCQNAGSTVYYPNEKDCETRGDEVFCDTAAGINVAEQSKEC

NINISTTNYPCKVSTGREPISMVALSPLGALVACYKGVSCSIOSNRVGII

KQLNKGCSYITNQDADTVTIDNTVYQLSKVEGEQHVIKGRPVSSSFDPVK

FPEDQFNVALDQVFENIENSQALVDQSNRILSSAEKGN<u>TGFIIVIILIAV</u>

<u>LGSSMILVSIFIIIKKTICKQTGAPPELSGVTNNGFIPHS</u>

In certain embodiments, the non-RSV sequences are not displayed on the surface of VLP (e.g., they form the transmembrane domain anchored in the scaffold of the VLP and/or the domain within the interior of the VLP).

The VLPs described herein also comprise a matrix protein from a pneumovirus, for example an hMPV matrix protein (M). An exemplary hMPV matrix protein is shown below:

Metapneumovirus M amino acid sequence: UniProtKB/
Swiss-Prot: Q6WB99.1 (SEQ ID NO: 3):
MESYLVDTYQGIPYTAAVQVDLVEKDLLPASLTIWFPLFQANTPPAVLL

DQLKTLTITTLYAASQSGPILKVNASAQGAAMSVLPKKFEVNATVALDE

YSKLEFDKLTVCEVKTVYLTTMKPYGMVSKFVSSAKPVGKKTHDLIALC

DFMDLEKNTPVTIPAFIKSVSIKESESATVEAAISSEADQALTQAKIAP

YAGLIMIMITSTNPKGIFKKLGAGTQVIVELGAYVQAESISKICKTWSH

QGTRYVLKSR

In one embodiment of the invention, the proteins displayed on the surface comprise one or more pneumovirus F proteins as described herein, which after expression leads to the formation of VLPs. In order to enhance assembly and release of these VLPs from the producing cells, for instance, hRSV and/or hMPV F may be co-expressed with the hMPV M protein and additional recombinant wild type or modified proteins from paramyxovirus such as: Nucleocapsid protein (N), Small Hydrophobic protein (SH), G protein, M2 protein, L polymerase protein, P protein and proteins.

In still further embodiments, the positional order of the protein-encoding segments may be inverted (with respect to each other) in any order. For example, the F protein(s) (e.g., RSV and/or MPV) may be genetically linked directly to the scaffold proteins (e.g., hMPV) in any order.

In still further embodiments, the VLPs and methods described herein may include changes in the sequence of the proteins (e.g., modifications to the nucleotide sequence which result in amino acid modifications), which can be used to enhance the formation and release of the VLP from the producing cells.

VLP Production

The production of VLPs as described herein may be achieved by any suitable method, including but not limited to transient and/or stable expression of the protein-encoding sequences in a suspension culture of eukaryotic cells, typically requiring a period of continued cell culture after which the VLPs are harvested from the culture medium. The VLPs produced as described herein are conveniently prepared using standard recombinant techniques. Polynucleotides encoding the VLP-forming protein(s) are introduced into a host cell and, when the proteins are expressed in the cell, they assembly into VLPs.

Polynucleotide sequences coding for molecules (proteins) that form and/or are incorporated into the VLPs can be obtained using recombinant methods, such as by screening cDNA and genomic libraries from cells expressing the gene, or by deriving the gene from a vector known to include the same. For example, plasmids which contain sequences that encode naturally occurring or altered cellular products may be obtained from a depository such as the American Type Culture Collection (A.T.C.C., Manassas, Va.) or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also PCR Technology: Principles and Applications for DNA Amplification, Erlich (ed.), Stockton Press, 1989)) using oligonucleotide primers complementary-to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311.

Preferably, the sequences employed to form VLPs as described herein exhibit between about 60% to 80% (or any value therebetween including 61%, 62%, 63%, 64%, 65%, 66%, 67%, 68%, 69%, 70%, 71%, 72%, 73%, 74%, 75%, 76%, 77%, 78% and 79%) sequence identity to a naturally occurring pneumovirus polynucleotide sequence and more preferably the sequences exhibit between about 80% and 100% (or any value therebetween including 81%, 82%, 83%, 84%, 85%, 86%, 87%, 88%, 89%, 90%, 91%, 92%, 93%, 94%, 95%, 96%, 97%, 98% and 99%) sequence identity to a naturally occurring polynucleotide sequence.

Any of the sequences described herein may further include additional sequences. For example, to further to enhance vaccine potency, hybrid molecules are expressed and incorporated into the sub-viral structure. These hybrid molecules are generated by linking, at the DNA level, the sequences coding for the protein genes with sequences coding for an adjuvant or immuno-regulatory moiety. During sub-viral structure formation, these hybrid proteins are incorporated into or onto the particle. The incorporation of one or more polypeptide immunomodulatory polypeptides (e.g., adjuvants describe in detail below) into the sequences described herein into the VLP may enhance potency and therefore reduces the amount of antigen required for stimulating a protective immune response. Alternatively, as described below, one or more additional molecules (polypeptide or small molecules) may be included in the VLP-containing compositions after production of the VLP from the sequences described herein.

These sub-viral structures do not contain infectious viral nucleic acids and they are not infectious eliminating the need for chemical inactivation. Absence of chemical treatment preserves native epitopes and protein conformations enhancing the immunogenic characteristics of the vaccine.

The sequences described herein can be operably linked to each other in any combination. For example, one or more sequences may be expressed from the same promoter and/or from different promoters. As described below, sequences may be included on one or more vectors. Non-limiting examples of vectors that can be used to express sequences that assemble into VLPs as described herein include viral-based vectors (e.g., retrovirus, adenovirus, adeno-associated virus, lentivirus), baculovirus vectors (see, Examples), plasmid vectors, non-viral vectors, mammalians vectors, mammalian artificial chromosomes (e.g., liposomes, particulate carriers, etc.) and combinations thereof. The expression vector(s) typically contain(s) coding sequences and expression control elements which allow expression of the coding regions in a suitable host. Enhancer elements may also be used herein to increase expression levels of the mammalian constructs.

Vaccine formulation is accomplished according to standard procedures, for example as shown in FIGS. 1 and 2.

In certain embodiments, the VLPs are monovalent in that they include one antigenic pneumovirus (e.g., RSV and/or MPV F or G) protein displayed on the surface of the VLP. In other embodiments, the VLPs are bi or multi-valent and display multiple pneumovirus (e.g., RSV and/or MPV F, G and/or SH) proteins on the surface the VLP. See, e.g., FIG. 2A.

Furthermore, combination vaccine can be created by blending in a single formulation monovalent, bivalent or multivalent compositions of a disease-causing virus (e.g. RSV and/or MPV) with composition of another disease-causing virus or other serotype such as another RSV serotype or hMPV VLPs.

The utility of the VLPs include, but it is not limited to, the generation of immunogenic (vaccine) compositions that when administered to humans are able to treat and/or prevent pneumovirus (e.g., RSV, MPV) infection, including treatment and/or prevention of infection with one and/or more pneumovirus virus clades antigenic variants or serotypes. Pneumovirus VLPs may be used in combination with other pneumovirus VLPs (e.g., different RSV serotypes or hMPV VLPs, etc.). The VLPs described herein can be also be used in diagnostic and therapeutic applications.

Suitable host cells for producing VLPs as described herein include, but are not limited to, bacterial, mammalian, baculovirus/insect, yeast, plant and Xenopus cells. For example, a number of mammalian cell lines are known in the art and include primary cells as well as immortalized cell lines available from the American Type Culture Collection (A.T.C.C., Manassas, Va.), such as, but not limited to, MDCK, BHK, VERO, MRC-5, WI-38, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 (such cell lines are available, for example, from the A.T.C.C.).

The immunogenicity of VLP vaccines may be affected by the structural conformation of the E protein displayed on the particles' surface. Changing the temperature of the fermentation process may alter this conformation. In one embodiment, the VLPs are produced at lower temperature (31° C., plus or minus 3 degrees centigrade) than the standard temperature of fermentation of 37° C. VLPs produced at the lower temperature when administered as vaccine may induce higher neutralizing antibody titers than those produced at 37° C.

The VLPs as described herein may be purified following production. Non-limiting examples of suitable purification (isolation) from the cell culture medium procedures include using centrifugation and/or gradient centrifugation under suitable conditions. Other methods of purification may include sequential steps of filtration and/or chromatography procedures including ion exchange, affinity, size exclusion and/or hydrophobic interaction chemistries.

Cell lines expressing one or more of the sequences described above can readily be generated given the disclosure provided herein by stably integrating one or more expression vector constructs encoding the proteins of the VLP. The promoter regulating expression of the stably integrated pneumovirus sequences (s) may be constitutive or inducible. Thus, a cell line can be generated in which one or more proteins are stably integrated such that, upon introduction of the sequences described herein (e.g., hybrid proteins) into a host cell and expression of the proteins encoded by the polynucleotides, non-replicating viral particles that present antigenic glycoproteins are formed.

In certain embodiments, a mammalian cell line that stably expressed two or more antigenically distinct pneumovirus (e.g., RSV) proteins is generated. Sequences encoding proteins can be introduced into such a cell line to produce VLPs as described herein. Alternatively, a cell line that stably produces structural proteins can be generated and sequences encoding the antigenic pneumovirus (e.g., RSV) protein(s) from the selected strain(s)/serotype(s)/clade(s) introduced into the cell line, resulting in production of VLPs presenting the desired antigenic glycoproteins.

The parent cell line from which a VLP-producer cell line is derived can be selected from any cell described above, including for example, mammalian, insect, yeast, bacterial cell lines. In a preferred embodiment, the cell line is a mammalian cell line (e.g., 293, RD, COS-7, CHO, BHK, MDCK, MDBK, MRC-5, VERO, HT1080, and myeloma cells). Production of VLPs using mammalian cells provides (i) VLP formation; (ii) correct post translation modifications (glycosylation, palmitylation) and budding; (iii) absence of non-mammalian cell contaminants and (iv) ease of purification.

In addition to creating stably transfected cell lines, pneumovirus-encoding sequences may also be transiently expressed in host cells. Suitable recombinant expression host cell systems include, but are not limited to, bacterial, mammalian, baculovirus/insect, yeast and *Xenopus* expression systems, well known in the art. Particularly preferred expression systems are mammalian cell lines, insect and yeast systems. Expression in mammalian and other systems can be achieved by multiple methods such as transfection or viral transduction using viral vectors such as: vaccinia, Semliki Forest virus (SFV), Alphaviruses (such as, Sindbis, Venezuelan Equine Encephalitis (VEE)), Retrovirus vectors (lentivirus) etc.

Many suitable expression systems are commercially available, including, for example, the following: baculovirus expression (Reilly, P. R., et al., BACULOVIRUS EXPRESSION VECTORS: A LABORATORY MANUAL (1992); Beames, et al., Biotechniques 11:378 (1991); Pharmingen; Clontech, Palo Alto, Calif.)), vaccinia expression systems (Earl, P. L., et al., "Expression of proteins in mammalian cells using vaccinia" In Current Protocols in Molecular Biology (F. M. Ausubel, et al. Eds.), Greene Publishing Associates & Wiley Interscience, New York (1991); Moss, B., et al., U.S. Pat. No. 5,135,855, issued Aug. 4, 1992), expression in bacteria (Ausubel, F. M., et al., CURRENT PROTOCOLS IN MOLECULAR BIOLOGY, John Wiley and Sons, Inc., Media PA; Clontech), expression in yeast (Rosenberg, S. and Tekamp-Olson, P., U.S. Pat. No. RE35, 749, issued, Mar. 17, 1998, herein incorporated by reference; Shuster, J. R., U.S. Pat. No. 5,629,203, issued May 13, 1997, herein incorporated by reference; Gellissen, G., et al., Antonie Van Leeuwenhoek, 62(1-2):79-93 (1992); Romanos, M. A., et al., Yeast 8(6):423-488 (1992); Goeddel, D. V., Methods in Enzymology 185 (1990); Guthrie, C., and G. R. Fink, Methods in Enzymology 194 (1991)), expression in mammalian cells (Clontech; Gibco-BRL, Ground Island, N.Y.; e.g., Chinese hamster ovary (CHO) cell lines (Haynes, J., et al., Nuc. Acid. Res. 11:687-706 (1983); 1983, Lau, Y. F., et al., Mol. Cell. Biol. 4:1469-1475 (1984); Kaufman, R. J., "Selection and coamplification of heterologous genes in mammalian cells," in Methods in Enzymology, vol. 185, pp 537-566. Academic Press, Inc., San Diego Calif. (1991)), and expression in plant cells (plant cloning vectors, Clontech Laboratories, Inc., Palo-Alto, Calif, and Pharmacia LKB Biotechnology, Inc., Pistcataway, N.J.; Hood, E., et al., J. Bacteriol. 168:1291-1301 (1986); Nagel, R., et al., FEMS Microbiol. Lett. 67:325 (1990); An, et al., "Binary Vectors", and others in Plant Molecular Biology Manual A3:1-19 (1988); Miki, B. L. A., et al., pp. 249-265, and others in Plant DNA Infectious Agents (Holm, T., et al., eds.) Springer-Verlag, Wien, Austria, (1987); Plant Molecular Biology: Essential Techniques, P. G. Jones and J. M. Sutton, New York, J. Wiley, 1997; Miglani, Gurbachan Dictionary of Plant Genetics and Molecular Biology, New York, Food Products Press, 1998; Henry, R. J., Practical Applications of Plant Molecular Biology, New York, Chapman & Hall, 1997).

When expression vectors containing the altered genes that code for the proteins required for sub-viral structure vaccine formation are introduced into host cell(s) and subsequently expressed at the necessary level, the sub-viral structure vaccine assembles and is then released from the cell surface into the culture media.

Depending on the expression system and host selected, the VLPs are produced by growing host cells transformed by an expression vector under conditions whereby the particle-forming polypeptide(s) is (are) expressed and VLPs can be formed. The selection of the appropriate growth conditions is within the skill of the art. If the VLPs are formed and retained intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990). Alternatively, VLPs may be secreted and harvested from the surrounding culture media.

The particles are then isolated (or substantially purified) using methods that preserve the integrity thereof, such as, by density gradient centrifugation, e.g., sucrose, potassium tartrate or Iodixanol gradients, PEG-precipitation, pelleting, and the like (see, e.g., Kirnbauer et al. J. Virol. (1993) 67:6929-6936), as well as standard purification techniques including, e.g., ion exchange and gel filtration chromatography, tangential filtration, etc.

Compositions

VLPs produced as described herein can be used to elicit an immune response when administered to a subject. As discussed above, the VLPs can comprise a variety of antigens (e.g., one or more modified pneumovirus antigens from one or more pneumoviruses and/or one or more strains, serotypes, clades or isolates of a particular pneumovirus such as RSV and/or MPV). Purified VLPs can be administered to a vertebrate subject, usually in the form of vaccine compositions. Combination vaccines may also be used, where such vaccines contain, for example, other proteins derived from other viruses or other organisms and/or gene delivery vaccines encoding such antigens.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 μg to about 10 (or more) mg, more preferably about 1 μg to about 300 μg, of VLP/antigen.

Sub-viral structure vaccines are purified from the cell culture media and formulated with the appropriate buffers and additives, such as a) preservatives or antibiotics; b) stabilizers, including proteins or organic compounds; c) adjuvants or immuno-modulators for enhancing potency and modulating immune responses (humoral and cellular) to the vaccine; or d) molecules that enhance presentation of vaccine antigens to specifics cell of the immune system. This vaccine can be prepared in a freeze-dried (lyophilized) form in order to provide for appropriate storage and maximize the shelf-life of the preparation. This will allow for stock piling of vaccine for prolonged periods of time maintaining immunogenicity, potency and efficacy.

A carrier is optionally present in the compositions described herein. Typically, a carrier is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly (lactide-co-glycolides), known as PLG. See, e.g., Jeffery et al., Pharm. Res. (1993) 10:362-368; McGee J P, et al., J Microencapsul. 14(2):197-210, 1997; O'Hagan D T, et al., Vaccine 11(2):149-54, 1993. Such carriers are well known to those of ordinary skill in the art.

Additionally, these carriers may function as immunostimulating agents ("adjuvants"). Exemplary adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, MT) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detoxu); (3) saponin adjuvants, such as Stimulon™. (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO 93/13202 and WO 92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Examples of suitable immunomodulatory molecules for use herein include adjuvants described above and the following: IL-1 and IL-2 (Karupiah et al. (1990) J. Immunology 144:290-298, Weber et al. (1987) J. Exp. Med. 166: 1716-1733, Gansbacher et al. (1990) J. Exp. Med. 172:1217-1224, and U.S. Pat. No. 4,738,927; IL-3 and IL-4 (Tepper et al. (1989) Cell 57:503-512, Golumbek et al. (1991) Science 254:713-716, and U.S. Pat. No. 5,017,691); IL-5 and IL-6 (Brakenhof et al. (1987) J. Immunol. 139:4116-4121, and International Publication No. WO 90/06370); IL-7 (U.S. Pat. No. 4,965,195); IL-8, IL-9, IL-10, IL-11, IL-12, and IL-13 (Cytokine Bulletin, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) Methods in Enz. 78:387-394, Twu et al. (1989) *Proc. Natl. Acad. Sci. USA* 86:2046-2050, and Faktor et al. (1990) *Oncogene* 5:867-872); (3-interferon (Seif et al. (1991) *J. Virol.* 65:664-671); γ-interferons (Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188); tumor necrosis factors (TNFs) (Jayaraman et al. (1990) *J. Immunology* 144:942-951); CD3 (Krissanen et al. (1987) Immunogenetics 26:258-266); ICAM-1 (Altman et al. (1989) *Nature* 338:512-514, Simmons et al. (1988) *Nature* 331:624-627); ICAM-2, LFA-1, LFA-3 (Wallner et al. (1987) *J. Exp. Med.*

166:923-932); MHC class I molecules, MHC class II molecules, B7.1-β2-microglobulin (Parnes et al. (1981) *Proc. Natl. Acad. Sci. USA* 78:2253-2257); chaperones such as calnexin; and MHC-linked transporter proteins or analogs thereof (Powis et al. (1991) *Nature* 354:528-531). Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids encoding one or more of the above-identified polypeptides can be digested with appropriate restriction enzymes, and DNA fragments containing the particular gene of interest can be inserted into a gene transfer vector (e.g., expression vector as described above) using standard molecular biology techniques. (See, e.g., Sambrook et al., supra, or Ausubel et al. (eds) Current Protocols in Molecular Biology, Greene Publishing and Wiley-Interscience).

Administration

The VLPs and compositions comprising these VLPs can be administered to a subject by any mode of delivery, including, for example, by parenteral injection (e.g. subcutaneously, intraperitoneally, intravenously, intramuscularly, or to the interstitial space of a tissue), or by rectal, oral (e.g. tablet, spray), vaginal, topical, transdermal (e.g. see WO99/27961) or transcutaneous (e.g. see WO02/074244 and WO02/064162), intranasal (e.g. see WO03/028760), ocular, aural, pulmonary or other mucosal administration and/or inhalation of powder compositions. Multiple doses can be administered by the same or different routes. In a preferred embodiment, the doses are intranasally administered.

The VLPs (and VLP-containing compositions) can be administered prior to, concurrent with, or subsequent to delivery of other vaccines. Also, the site of VLP administration may be the same or different as other vaccine compositions that are being administered.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the potency of the modality, the vaccine delivery employed, the need of the subject and be dependent on the judgment of the practitioner.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting. Thus, it will be apparent that while exemplary results are presented with respect to RSV antigen proteins, the teachings herein are equally applicable to any pneumovirus.

EXAMPLES

Example 1

Pneumovirus VLP Production

Respiratory Syncytial Virus (RSV) is the leading cause of severe respiratory disease in infants and children and represents an important health burden for the elderly and the immunocompromised globally. In spite of decades of research efforts, no licensed vaccine is available for RSV.

We have developed virus-like particle (VLP) based RSV vaccines assembled with the human metapneumovirus matrix protein (hMPV M) as the structural scaffold and the RSV fusion glycoprotein (F) in either the prefusion or postfusion conformations as its prime surface immunogen. Vaccines were composed of prefusion F, postfusion F or a combination of both conformations, and formulated with the squalene-based oil emulsion as adjuvant. Immunization with these VLP vaccines afforded full protection against RSV infection and prevented detectable viral replication in the mouse lung after challenge. Analysis of lung cytokines and chemokines showed that VLP vaccination mostly induced production of IFN-γ, marker of Th1-mediated immune response, which is predominantly required for viral protection. Conversely, immunization with a formalin inactivated RSV (FI-RSV) vaccine induced high levels of inflammatory chemokines and cytokines of the Th2 and Th17 types of immune mediated responses, as well as severe lung inflammation and histopathology. The VLP vaccines showed restricted production of these immune mediators and did not induce severe bronchiolitis or perivascular infiltration as seen with the FI-RSV vaccine. Remarkably, analysis of the serum from immunized mice showed that the VLP vaccine formulated using a combination of prefusion and postfusion F elicited the highest level of neutralizing antibody and enhanced the Th1-mediated immune response.

Human Respiratory Syncytial Virus (RSV) is the leading cause of severe pediatric pulmonary disease worldwide. RSV infects nearly all infants at least once by the age of 2 years. Epidemiological studies around the globe indicate that 2-5% of the children infected with RSV require hospitalization with the most severe morbidity and mortality disproportionality affecting premature infants. RSV disease causes 100,000 to 200,000 fatalities per year globally (1, 2). It is believed that severe RSV infection can predispose children to develop wheezing with future illnesses and potentially asthma (3, 4). RSV infection elicits neutralizing antibodies and a T-cell response that wanes over time, consequently the patient is often unprotected against reinfection (5, 6). Furthermore, elderly people show a greater risk of severe RSV disease upon reinfection (7). Despite decades of research efforts, no licensed vaccine is currently available to control or prevent RSV infection (8). Vaccinology research shows that the F glycoprotein is the most attractive target for eliciting neutralizing antibodies against the virus. RSV displays different conformations of F that are antigenically distinct: the highly stable postfusion, and the metastable prefusion (9). Magro et. al. (10) have demonstrated that antibodies specific to prefusion F account for most of the neutralizing activity in a prophylactic human Ig preparation and immunized rabbits. Subsequently, McLellan and coworkers (9) determined the protein structure of the prefusion F by X-ray crystallography and identified the prefusion-only antigenic site φ (FIG. 1A). While Palivizumab can recognize both postfusion and prefusion structures, a subset of highly neutralizing antibodies 5C4, AM22 and D25 bind specifically to the prefusion antigenic site φ (9, 10). Interestingly, AM14 and MPE8 neutralizing antibodies are also able to very efficiently recognize the prefusion F using alternative antigenic sites. This demonstrates that the prefusion F expresses multiple epitopes suitable for target therapy (11, 12), which are not exhibited in the postfusion conformation.

Adopting structural vaccinology, our group has developed virus-like particle (VLP) vaccines containing recombinant postfusion and prefusion F hybrids together with the human metapneumovirus (hMPV) matrix protein (M). Efficacy studies showed that immunization with prefusion F VLP, postfusion F VLP or a combination of both, afforded complete protection against an RSV virus challenge. Importantly, VLP vaccination was safe and effective in stimulating a Th1 type cytokine profile and the combo VLP vaccine elicited the highest-level of IgG2a antibody and neutralization activity.

A. Materials and Methods
Structural Vaccinology

The RSV fusion (F) (GenBank: ACO83302.1) and human metapneumovirus matrix (M) (GenBank: AIY25728.1) genes were codon optimized and chemically synthesized (Blue Heron Biotech, WA). Prefusion F mutants were designed by protein structure analysis using the Cn3D software (NCBI, MD) and data from NCBI repository (9, 13). Wild type optimized RSV F was subcloned into an expression vector and mutagenized by cysteine substitutions using the QuickChange II kit (Agilent, CA) and DNA oligos (IDT, TX). The cytoplasmic tail (CT) and the transmembrane domain (TM) of RSV F was swapped with hMPV F analogs domains using recombinant DNA methods: hRSV F sequence from amino acids 1-524 (GenBank: AC083302.1, SEQ ID NO:1) was joined to the hMPV F sequence from amino acids 489-539 (GenBank: AEK26895.1, SEQ ID NO:2). Constructs were fully sequenced for quality verification.

Vaccine

RSV virus-like particles (VLPs) were produced in a suspension culture of mammalian cells following transient transfection of the VLP protein expression plasmids. Expi293F cells were maintained in serum free Expi293 expression medium (Life Technologies, CA). Transfection reaction was assembled in separate tubes: 1.0 μg DNA vectors, 3.0 μg of 25 kDa linear polyethylenimine (PEI) (Polysciences, PA), and 0.1 ml OptiMem, for each 1 ml of cells culture ($2.5\times10^6$ cells/ml). The plasmid for RSV F and HMPV M were transfected at a ratio of 70% and 30% respectively. The mixture was incubated for 15 min at room temperature and then added to the cells. Forty-eight hours after transfection, the culture supernatant was clarified by centrifugation at 8,000×g for 10 min. and VLPs concentrated by ultracentrifugation for 2 hours at 140,000×g using a SW 28 rotor (Beckman Coulter CA). Pellets were resuspended in 250 μl of buffer E (250 mM Sucrose, 100 mM $MgSO_4$, 10 mM TRIS pH 7.5) containing protease inhibitors (Thermo Scientific, MA). The VLPs were subsequently purified by ultracentrifugation through a continuous sucrose gradient (10%-50%) for 4 hours at 180,000×g using a SW 40Ti rotor. The VLPs were collected from the 15%-25% fraction and further purified by ultrafiltration using Vivaspin system 100 kDa cut-off (Sartorious, NY).

The VLPs were characterized by Western blot, dot blot, and electron microscopy. The VLP combo vaccine was prepared by blending equal amounts (2 μg of F content) of VLPs with prefusion F and postfusion F per dose (4 μg total F content). FI-RSV vaccine was produced using the protocol described by Prince at. al. (14). The final preparation was adjuvanted with Imject Alum (Thermo Scientific, MA) to a final concentration of 4 mg/ml of Aluminium Hydroxide and then diluted 1:25 in PBS for animal administration.

Dot Blot and Western Blot

The immune reactivity and antigen concentration of the VLP vaccine was assayed using a dot blot assay. VLP samples in a volume of 1-5 μl were absorbed into nitrocellulose for 15 min and then blocked for 1 hr with 3% non-fat dry milk in Tris-buffered saline plus 0.1% Tween-20 (TBS-Tween). Primary antibodies were: Palivizumab (Synagis®, MedImmune, MD), 131-2a (EMD-Millipore, MA), 5C4 (9) or anti-hMVP M (GeneTex clone 4821, CA). Horseradish peroxidase (HRP) conjugated mouse anti-human antibody, or goat anti-mouse antibody were used as secondary antibody. Detection was performed using ECL substrate and digital imaging system (FluorChem M System, ProteinSimple CA). The dot blot with Palivizumab was used for quantifying F content in the vaccines as compared to a serial dilution of recombinant RSV F protein standard (Sino Biological, PA) and quantified using AlphaView SA imaging software (ProteinSimple, CA). Western blot was performed using Novex gel system (Life Technologies, CA) and Nupage 4-12% Bis-Tris Gel (Life Technologies, CA).

Electron Microscopy Analysis of the VLP particles

The VLP particles were examined by negative staining and electron microscopy (Zeiss 902 TEM, U=80 kV). 5 μl of resuspended particles were applied to a formvar coated copper grid FCF300-Cu (Electron Microscopy Science, PA) and stained with 2.0% of phosphotungstic acid, pH 7.0. Immunogold labeling was performed as follows: 5 μl of resuspended samples were applied to formvar-coated grids and incubated for 5 min at room temperature (RT). The grid was then washed 5 times with buffer (0.1% FBS in PBS, 10 mM glycine, 0.01% $NaN_3$); fixed with 4% paraformaldehyde in PBS for 15 min, and blocked in 1% BSA in PBS for 30 min. The sample was floated onto 40 μl of Palivizumab (Synagis, MedImmune MD) at 1:1000 dilution in 0.1% BSA in PBS+0.01% of $NaN_3$ buffer overnight at 4° C. The grid was then placed in a humid chamber to prevent evaporation. Following 5 washes with buffer, the grid was placed on a drop of 6 nm gold beads conjugated with goat anti-human polyclonal IgG antibody, (Abeam, MA), 1:3 dilution in 0.1% BSA in PBS+0.01% of $NaN_3$ for 2 hours at RT. Then sample was washed 5 times in washing buffer and stained with 2.0% of phosphotungstic acid, pH 7.0.

Virus Production and Titration

This study was performed in compliance of BSL-2 regulations. The RSV A2 strain was obtained from the ATCC- VR-1540 (ATCC, VA) and used for murine challenge, production of FI-RSV vaccine, immunization and viral assays. RSV was propagated in HEp-2 cells (ATCC VA, CCL-23) and using culture-medium DMEM with 2% fetal bovine serum (FBS) (Life Technologies CA) according to the supplier protocol. Viral titration was performed by plaque assay using HEp-2 monolayer. HEp-2 cells were infected for 1-hour for viral absorption with 10-fold serially diluted virus in serum free DMEM medium, from $10^4$ to $10^8$ dilution range. Subsequently, an overlay of 1% methylcellulose (Sigma-Aldrich MO, C-4888) in DMEM medium supplemented with 2% FBS was applied to each well to prevent viral particles diffusion. After 4 to 5 days of incubation the overlay was removed and cells were fixed using cold methanol for 20 min, at −20° C. Virus plaques were stained by immunocytochemistry techniques using an anti-RSV goat antibody (EMD-Millipore Corporation CA, AB1128) diluted 1:500 in blocking buffer as a primary antibody. Immune detection was performed using HRP conjugated rabbit anti-goat antibody (Abcam MA, ab97105) as a secondary antibody. Immunostaining was developed using DAB Peroxidase (HRP) Substrate Kit (Vector Laboratories CA, SK-4100) and plaques were counted using a light microscope with 4× to 20× objective magnification.

Murine Model for Immunization and RSV Infection

BALB/c mice (*Mus musculus*) 6-week-old females from Charles River were housed at the Department of Comparative Medicine, New York Medical College, Valhalla, N.Y. Mice were anesthetized with Ketamine (100 mg/kg)/Xylazine (10 mg/kg) administered via intraperitoneal injection before immunization or blood collection. Mice were immunized by intramuscular (IM) injection with 50 µl of postfusion, prefusion or the combo VLP vaccines as well as FI-RSV, and placebo control (n=10 per group). Immunizations were administered at day 1 and 14 and each VLP vaccine dose contained 4 µg of total recombinant RSV F admixed in a 1:1 volume with a squalene-based oil-in-water nano-emulsion AddaVax (InvivoGen, CA). The placebo group received PBS admixed with AddaVax at 1:1 volume. Serum was collected by retro-orbital bleeding before and after immunization. Mice were challenged with 1×10$^6$ pfu of RSV A2 strain contained in a 50 µl administrated via the intranasal route as small drops (Pipetman with ultraslim tip) at day 28. Group of mice were euthanized at 4, and 7 days post challenge for lung and blood harvest (S. FIG. 2).

Pulmonary RSV Quantification by Plaque Assay

Lungs from RSV infected mice were harvested, weighed, and homogenized using an Omni tissue homogenizer (Omni International) in Opti-MEM I media containing 25% sucrose, penicillin-streptomycin-glutamine (Life Technologies, CA), and 2.5 µg/ml Fungizone (Chem-Impex International Inc., IL). Lung supernatants were obtained by centrifugation and viral titer measured by plaque assay as above.

Neutralization Assay

Plaque reduction neutralization assays (PRNT) were performed in duplicate using serum samples collected before viral challenge (day 28). Serial dilution of serum was incubated with 100 pfu of RSV A2 virus for 1 hour at 37° C. and neutralization power measured by a plaque assay in HEp-2 as described above. $IC_{50}$ calculation was performed applying the Probit analysis (15).

Luminex Cytokines and Chemokines Analysis

Magnetic bead-based sandwich immunoassays for cytokines using MILLIPLEX MAP multiplex Mouse Cytokine Panel 1 (EMD-Millipore, MA) were performed according to the manufacturer's instruction. Lung samples (25 µl) were analyzed in duplicate wells using a Luminex MagPix (Luminex Corp., TX). Cytokine concentrations were determined by Luminex Xponent 4.2 and EMD-Millipore Milliplex Analyst v5.1 using 5-p log analysis. IFNγ analysis in lung fluids was confirmed using an ELISA Kit (eBioscience, CA).

ELBA Analysis of IgG Subtypes

Each well of ELISA assay plates (Corning Costar NY, 3912) was coated with RSV A2 strain containing 100 ng of F protein content determined by dot blot analysis using purified recombinant F protein (Sino Biological, PA) as standard, and incubated at 4° C. overnight (see above). Serum samples were serially diluted in blocking buffer (5% milk in TBS-tween), applied in triplicated to the ELISA plates and incubated for 2 hours at room temperature. Following washes, detection was carried out using the following antibodies: IgG1 subtype (Jackson ImmunoResearch Lab. PA, 115-035-205), IgG2a subtype (Jackson ImmunoResearch Lab. PA, 115-035-206). The ELISA measurements were performed using chemiluminescence (ECL) method and microplate reader (BioTek VT, Synergy H1). Endpoint calculation for ELISA assay was performed according to Frey et. al. (16).

Histopathology

Lungs were harvested on day 4 post-infection and fixed in 10% buffered formalin phosphate. Lung samples were processed at the Department of Pathology at the New York Medical College (Valhalla, NY) and stained with hematoxylin and eosin (H&E) following a standard protocol (17). Examination and scoring of lung histopathology was performed by blind evaluation of the H&E slides.

Statistics

Data was statistically analyzed and graphed using GraphPad Prism (GraphPad Software CA), and errors bars are representing calculated standard error. Statistical significance of the data was measured by one-way ANOVA test with Dunnett's multiple comparisons between experimental conditions, and t-test. Analysis of the ratio of IgG2a versus IgG1 was achieved using Taylor expansion statistical approach for calculating standard errors. Pictures and images were represented using Adobe Photoshop (Adobe, CA).

Example 2

Development of Recombinant RSV F Exhibiting Postfusion and Prefusion Conformations Structural analysis of the postfusion F shows that the C-terminus of F2 is in the opposite orientation and distant from the N-terminus of F1 (FIG. 1B), whereas these domains are adjacent in the prefusion conformation (9, 13). We identified within this region several amino acids that are in close proximity separated by less than 10 Angstroms. Based on this analysis, we generated 9 recombinant constructs with alternative disulfide bonds between these domains to stabilize F in its prefusion conformation and one with the furin cleavage site mutated (FIG. 7).

Figure 7C:
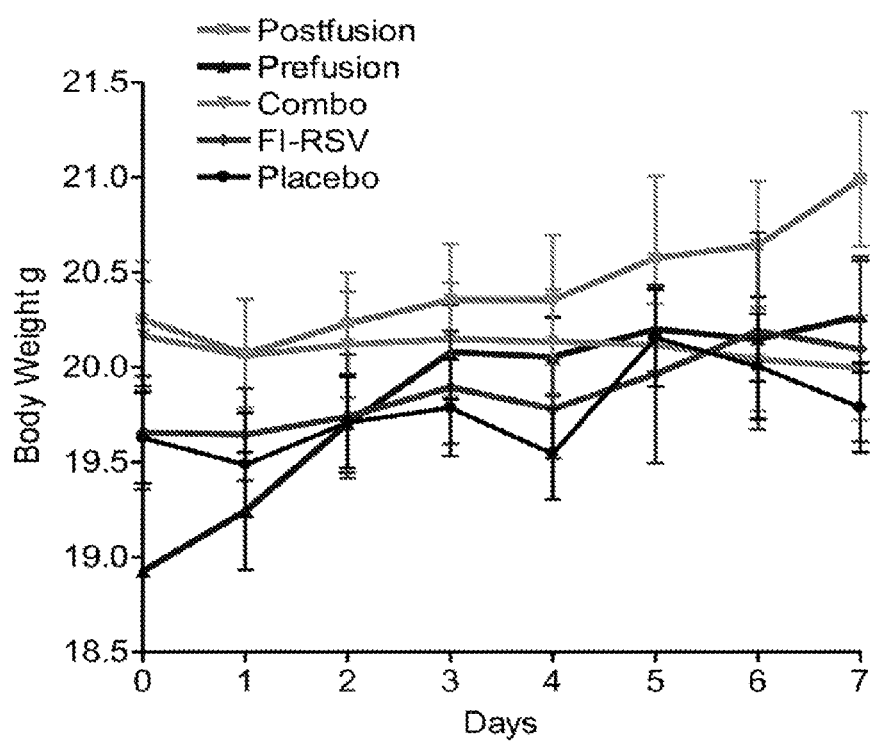

Prefusion F VLPs were produced in mammalian cells and analyzed by dot blot with the mAbs Palivizumab (antigenic site II) to measure F protein expression, and 5C4 to assess the presence and stability of the antigenic site φ (FIG. 7). We evaluated the postfusion state with the mAb 131-2a which is specific for the antigenic site I (FIG. 7). We found that the most stable prefusion F contained an intra-chain disulfide bond inside the F1 subunit described by McLellan et. al. (S155C/S290C) (18), plus an inter-chain disulfide bond between the F1 and F2 subunits with the cysteine substitutions: A102C and I148C (FIGS. 1A and 1B). By dot blot analysis with 5C4, we found that the prefusion F recombinant is recognized 19.2+/−2.4 fold more than the postfusion F (FIG. 1C). To assess whether the disulfide bridge A102C/I148C enhanced the stability of F prefusion, we tested an intermediate mutant having only one cysteine change, A102C. Indeed the mutant A102C construct demonstrated reactivity with 5C4 equivalent to wild type F postfusion construct. I In addition, dot blot analysis demonstrated that the combination of disulfide bonds S155C/S290C with A102C/I148C enhances 5C4 reactivity with respect to the single disulfide bond constructs (FIG. 7). VLPs assembled with this mutant (S155C/S290C plus A102C/I148C) were used in the vaccine studies. In addition, this F construct contains the cytoplasmic tail domain of HMPV F (FIG. 1A), which seems to further stabilize the structure of F incorporated in the particles as reflected by strong reactivity with 5C4 and Palivizumab (FIG. 1C). This and other mutants without the HMPV F tail demonstrated strong reactivity with 5C4 but weaker reactivity with Palivizumab (FIG. 7).

Example 3

Generation of VLPs Displaying RSV F Postfusion or Prefusion Conformations

The RSV envelope displays three virally encoded and membrane anchored proteins F, G and SH (FIG. 2A) (19). Underlying the envelope resides the matrix (M) protein, which during morphogenesis multimerizes and drives virion assembly and budding (20). To assemble VLPs, we utilized the RSV F either prefusion or postfusion together with the matrix protein (M) of the human metapneumovirus (hMPV) as scaffold, which as we found is more efficient than the RSV M in VLP formation. To optimize the interaction of RSV F and hMPV M, we replaced the cytoplasmic domain of the RSV F protein with the analogous domain of the hMPV F protein, which based on yield analysis in comparison to unmodified F demonstrated to enhance RSV F recruitment and incorporation onto the VLP surface (FIG. 1C).

Analysis of purified VLPs by Western blot showed that the RSV F hybrid co-purified with the hMPV M (FIG. 2B) and that replacement of the cytoplasmic tail enhanced incorporation of the RSV F into particles as compared to wild type RSV F.

These results suggest that the RSV F hybrids interact with the hMPV M via its engineered cytoplasmic domain. Examination of purified VLPs by electron microscopy (EM) showed spherical structures of ~80 nm in diameter that display F spikes protruding from the membrane envelope (FIGS. 2C and D). Immuno-gold labeling EM confirmed that the spikes were indeed composed of the glycoprotein F (FIG. 2D).

Example 4

Efficacy Evaluation of RSV F VLP Vaccines in a Murine Model

To assess the VLP vaccines protective efficacy, BALB/c mice were immunized twice with formulations containing either i) postfusion F VLPs, ii) prefusion F VLP, or iii) a combination of both VLPs (combo), and then challenged with RSV (FIG. 7). To evaluate the safety of the VLP vaccines, we included a group of mice immunized with the FI-RSV vaccine expected to induce vaccine-enhanced disease. Analysis of protective efficacy on day 4 post-challenge showed that the VLP immunized mice were completely protected from RSV replication and did not show a detectable viral load (<50 pfu/gram of lung tissue), whereas the placebo group demonstrated high levels of infective particles inside their lungs (75,000 pfu/gram of lung tissue) (FIG. 3).

Figure 3A:
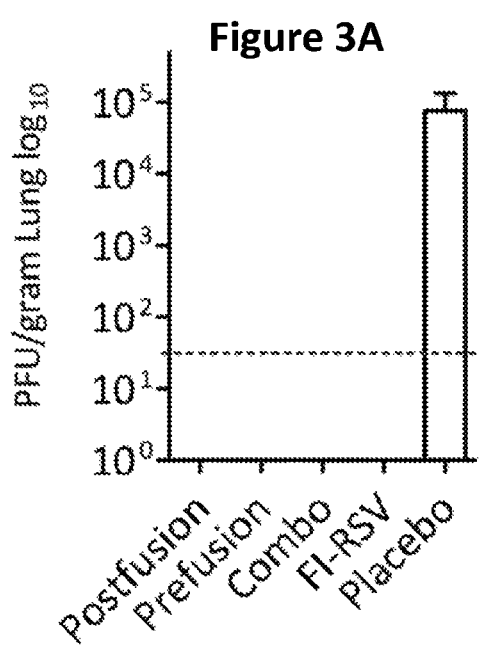
FIGS. 3A through 3D show VLPs vaccine protects against RSV infection.
Figure 3B:
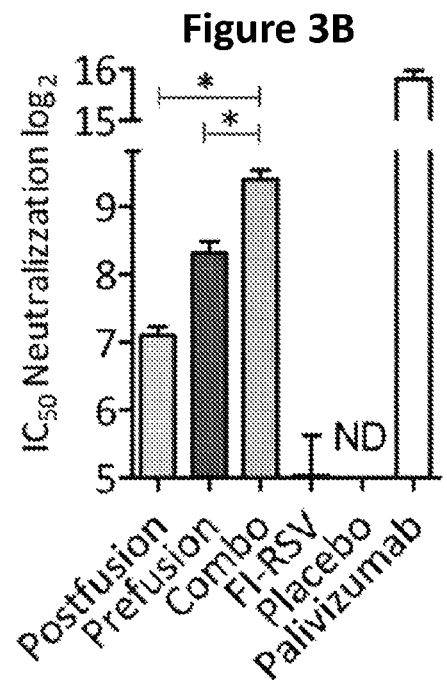

Assessment of viral load at day 7 post-challenge demonstrated the absence of replicating virus in the lungs of all the animals (data not shown). To appraise the quality and magnitude of the antibody response, we measured serum neutralizing activity of immunized animals prior to viral challenge (day 28) by plaque reduction neutralization test (PRNT) (FIG. 3B). This analysis showed that the combo VLP vaccine (prefusion plus postfusion F) elicited the highest level of neutralizing antibodies as compared to either the prefusion or postfusion F single vaccine formulations. The prefusion F VLP vaccine, however, elicited higher neutralizing antibody titers than the postfusion, results that agree with previous reports (21, 22). On the other hand, the FI-RSV vaccine failed to induce an appreciable level of neutralizing antibodies. The Palivizumab control demonstrated an $IC_{50}$ neutralizing activity of 2 µg/ml, a value that is similar to previous determinations (23).

Example 5

VLP Vaccine Stimulates a Balanced IgG Response

Figure 3C:
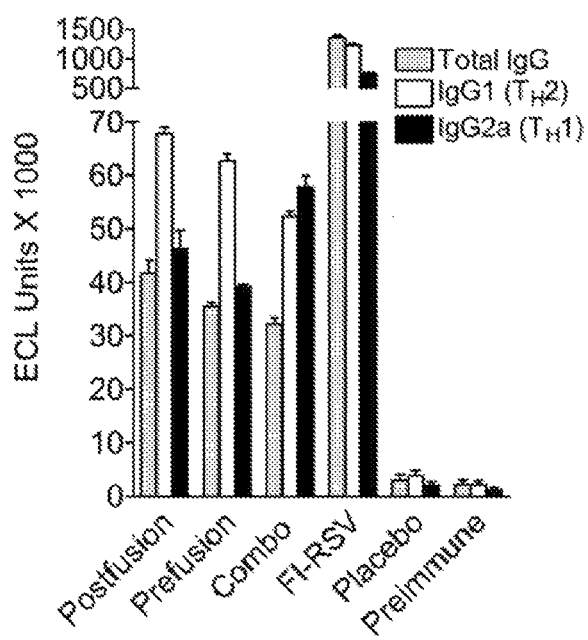
Figure 3D:
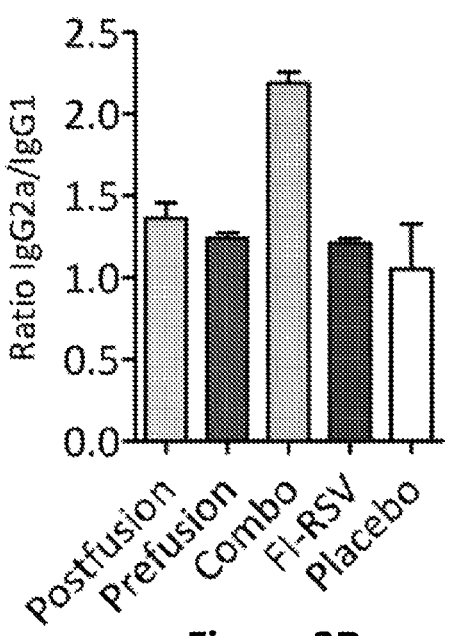

We assessed the magnitude of the IgG2a and IgG1 serum responses, which are correlates of Th1 and Th2 development respectively (FIGS. 3C and 3D). Mice that received VLP vaccine demonstrated induction of robust serum IgG responses as compared to the preimmune samples. On the other hand, serum from FI-RSV immunized mice showed the highest level of IgGs induction suggesting that antibodies toward multiple viral proteins were produced and detected in the whole virus ELISA. Analysis of IgG subtype demonstrated that the combo vaccine elicited a balanced Th1-versus Th2-mediated response, associated with a greater IgG2a versus IgG1 ratio (FIG. 3D).

As expected, placebo control demonstrated background levels of total and specific IgGs against RSV.

Example 6

Figure 4A:
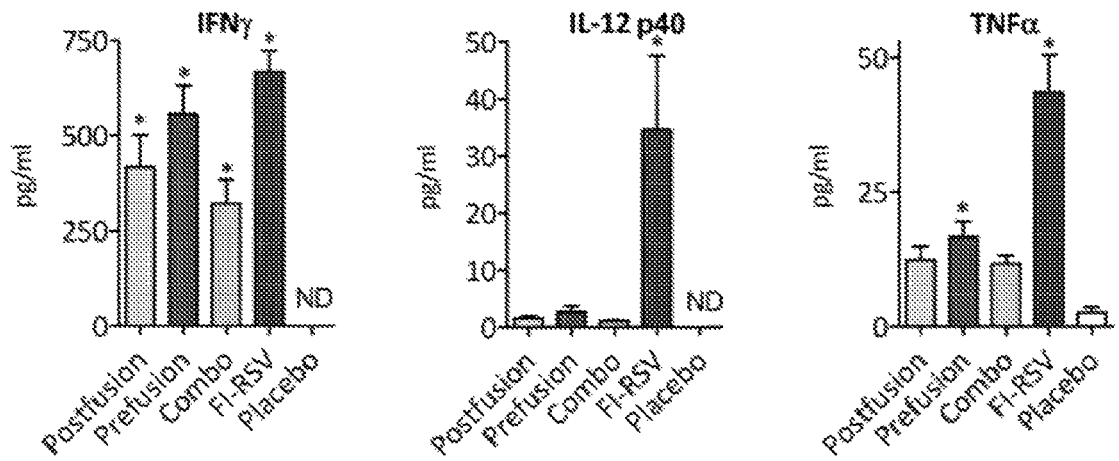
Figure 4B:
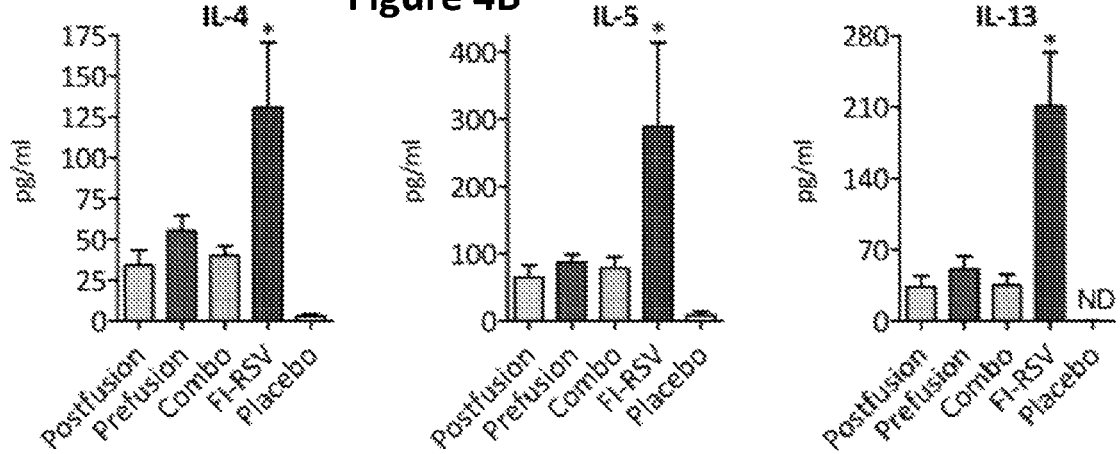
Figure 4B:
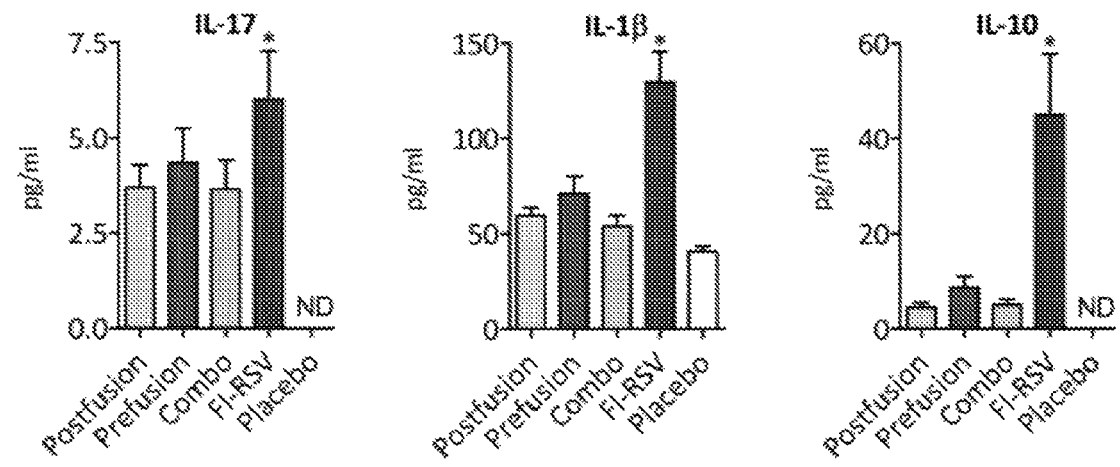
Figure 5A:
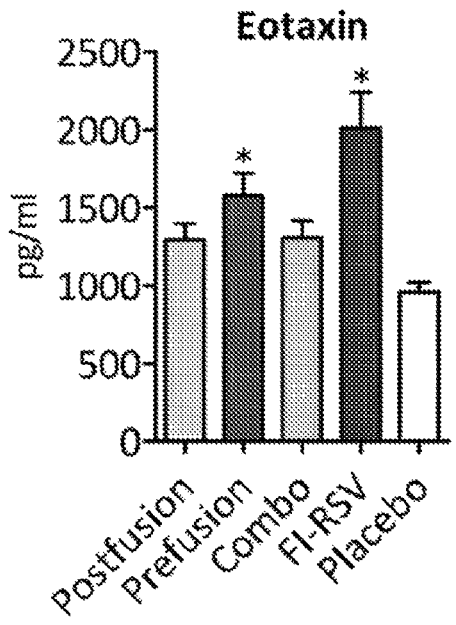
FIGS. 5A through 5D show chemokine responses in VLP vaccinated mouse lung after RSV infection. Analysis includes Eotaxin (FIG. 5A), MCP-1 (FIG. 5B), MIP-1α (FIG. 5C), and RANTES (FIG. 5D). Results were generated using a group of 4 mice per each condition 4 days post-infection; the asterisk indicates a statistically significant difference between an experimental condition and the placebo control.
Figure 5B:
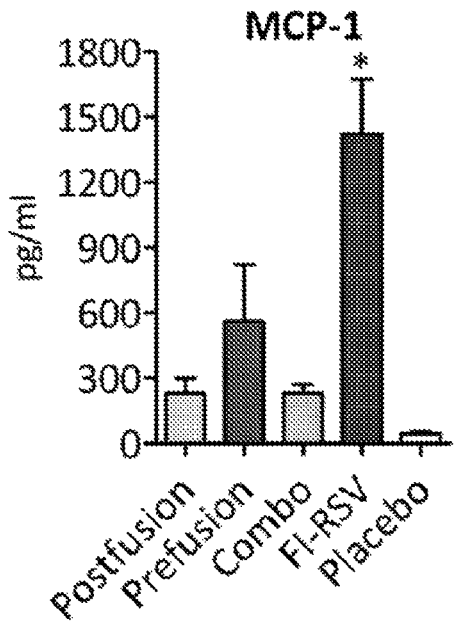
Figure 5C:
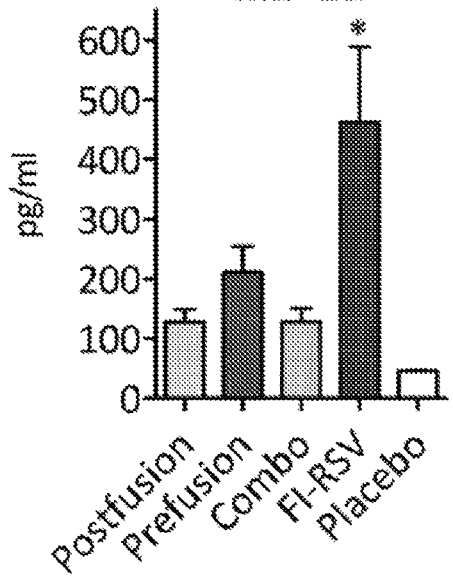
Figure 5D:
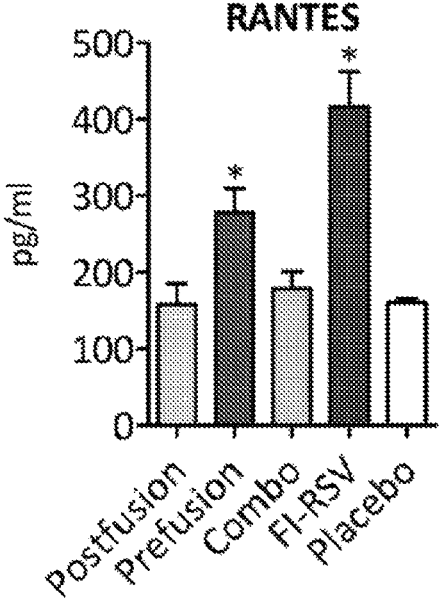

Analysis of the Cytokine Profile in VLP Vaccinated and Control Mice After RSV Infection We applied Luminex technology to study the cytokine and chemokine levels in lung homogenates of VLP vaccinated and control mice four days after challenge. We evaluated cytokine markers that correlate with Th1, Th2, and the Th17 type of immune responses as well as IL-10 (FIGS. 4A, 4B, 4C and 4D). VLP immunized mice showed a robust IFN-γ response in comparison to the placebo control (FIG. 4A). On the other hand, immunization with the FI-RSV vaccine stimulated a strong cytokines response that qualitatively and quantitatively differed from the one elicited in mice immunized with the VLP vaccine or placebo. We found that FI-RSV immunization induced high levels of the cytokines IFNγ, TNFα, IL-4, IL-10, IL-17 and IL-1β all of which have been associated with the exacerbation of RSV disease (24-29) (FIGS. 4A, 4B, 4C and 4D). In contrast, multiplex analysis of placebo control demonstrated very low expression of these cytokines indicating that RSV replication did not trigger or perhaps curtailed production of these immune signaling molecules (FIGS. 4A, 4B, 4C, and 4D). This is in agreement with Lambert and coworkers (30), who also found very low levels of IFNγ, IL-5, IL-13 and IL-17 in the lung of the placebo group at day 4 post challenge. However, higher doses of challenging virus (e.g. $1 \times 10^7$ PFU) increases the level of secreted cytokines as described by Rutigliano et. al. (29).

Chemokines recruit inflammatory cells to the infected tissue and are particularly elevated in bronchiolitis (31, 32). Thus, we analyzed Eotaxin, MCP-1, MIP-1α, and RANTES, all of which are involved in lung immune cell infiltration during bronchiolitis (FIG. 5). While FI-RSV vaccine strongly augmented each chemokine, the VLP immunized animals had a less significant induction of these inflammatory mediators, which were closer to that seen in the placebo control.

Example 7

Evaluation of VLP Vaccine Safety by Lung Histopathology Examination

VLP vaccine safety and tolerability was further evaluated by histological examination of lung tissue of VLP vaccinated mice after 4 days postinfection (FIGS. 6A and B). Placebo control mice that received a primary infection with $10^6$ pfu of RSV experienced some interstitial cellular infiltrate but limited or no sign of perivascular infiltration at day 4 post-challenge, indicating that virus replication was tolerated without provoking serious lesions. Indeed, a previous report (30) has shown minimal eosinophilic infiltration in primary infected mice under the same experimental conditions.

FI-RSV vaccinated mice displayed a massive perivascular, peribronchial and interstial infiltration of inflammatory cells. In contrast, the VLP immunization showed a limited immune cell infiltration. Blinded scoring of perivascular infiltration demonstrated that the combo VLP vaccine had the lowest level of histological changes (FIG. 6B). The perivascular infiltration in the prefusion and postfusion vaccine groups was more pronounced than that of the placebo control; however the overall lung architecture was not significantly different amongst these groups. Severe RSV disease and FI-RSV vaccine-enhanced disease are characterized by cellular infiltration and lung hyperinflation (33, 34). We found that lungs from mice immunized with FI-RSV were significantly larger and were >30% heavier than lungs from the placebo controls, while lungs from VLP vaccinated mice did not differ from the placebo group (FIG. 6C).

In sum, the data demonstrate the immunogenicity, efficacy and safety of a novel VLP based RSV vaccine constructed with different conformations of the RSV F glycoprotein. Previously tested subunit vaccines were formulated primarily with RSV F in its postfusion conformation (35, 36). Recent studies (21, 22, 37) however, have demonstrated that the RSV F in prefusion conformation has the ability to elicit higher levels of neutralizing antibodies than the postfusion conformation. Indeed, different groups have shown that vaccines containing RSV F in the prefusion conformation were superior in protecting mice and cotton rats from RSV infection (21, 22, 37). Considering these data, we designed, produced and tested a novel recombinant stabilized prefusion F that is highly expressed in mammalian cells, is incorporated into VLPs, and is recognized strongly by the 5C4 mAb, which binds the prefusion-only antigenic site ϕ.

Although VLPs are strong immunogens, we included an adjuvant in the VLP vaccine in order to elicit the greatest immunogenicity. Protection against RSV may require a greater immunity than that stimulated by natural infection, which does not prevent reinfection. We selected the squalene-based oil emulsion because it is a potent inducer of both Th1- and Th2-mediated immunity, is well tolerated and safe (38, 39).

Assessment of the protective efficacy afforded by VLP vaccination after RSV virus challenge showed that each one of the three VLP vaccine formulations protected the lungs from viral infection. Furthermore, evaluation of serum neutralization potency showed that the prefusion F VLP vaccine induced antibodies with higher neutralization power than did immunization with the postfusion F VLP vaccine in agreement with previous studies (21, 22), although not to the same extent. However, the VLP combo vaccine showed the best neutralization activity reaching a neutralizing power that was >4 fold greater than that seen with the postfusion VLP vaccine, and >2 fold greater than that seen with the prefusion VLP vaccine. Notably, all VLP vaccines contained the same total F protein content (4 μg total), suggesting that the combination of the two conformations of F protein may be synergistic in eliciting a protective immune response. Recent studies performed with the Newcastle disease virus VLP vaccines showed similar results when comparing prefusion and postfusion forms, however a combo formulation was not tested (21, 40). It seems reasonable that the combo vaccine displays a larger repertoire of neutralizing epitopes than either of its components. This outcome is significant for RSV vaccine development and requires further investigation to define the underlying mechanism.

Consistent with the antibody neutralization assay data, the IgG isotyping analysis showed that the combo vaccine induced a balanced Th1-mediated immune response. On the other hand, the FI-RSV vaccine elicited high levels IgG that did not correlate with the induction of neutralizing antibodies. This outcome clearly illustrates the dichotomy between high antibody titers and neutralizing capacity, which has been the hallmark of the FI-RSV vaccine enhanced disease.

Cytokine analysis showed that all VLP vaccinated mice produced statistically significant levels of IFNγ as compared to placebo, which is a correlate of induction of a Th1 type of immune response. On the other hand, the FI-RSV vaccine induced high levels of IFNγ, and TNFα, as well as a high production of Th2 polarizing cytokines (IL-4, IL-5 and IL-13), Th17 polarizing cytokines (IL-17, IL-1β) and IL-10, and chemokines (Eotaxin, MCP-1, MIP-1α, and RANTES) all of which have been associated with enhanced RSV pathogenesis (24-29). In contrast, VLP vaccinated mice produced much lower amounts of these inflammatory cytokines and chemokines. Furthermore, histopathology studies showed that VLP vaccination did not induce the detrimental immune cell infiltration inside the lung and that the VLP combo formulation was, in this regard, the best tolerated vaccine.

In summary, we describe the production of RSV VLPs composed of RSV F glycoprotein that display different epitopes suitable for the elicitation of neutralizing antibodies. Considering the diversity, neutralizing strength and distribution of epitopes both shared and unique, between the two conformations of F, it seemed important to compare the immunogenicity and efficacy of single VLP vaccines (prefusion or postfusion F) with a combo formulation. This study showed that the VLP combo vaccine, comprised of the multiple epitopes revealed in the prefusion and postfusion F, afforded complete protection against RSV and elicited production of the highest level of serum neutralizing antibodies that correlate with the development of a strong Th1-immune response. Furthermore, immunization with this vaccine proved to be safe, a condition that must be satisfied by any RSV vaccine candidate. We anticipate that the VLP combo vaccine may elicit a broader spectrum of neutralizing antibodies and thus afford better protection against RSV and is a viable safe and efficacious candidate for clinical evaluation.

REFERENCES

1. Meng J, Stobart C C, Hotard A L, Moore M L. An overview of respiratory syncytial virus. PLoS Pathog. 2014; 10: e1004016. doi:10.1371/journal.ppat.1004016
2. Hall C B, Weinberg G A, Iwane M K, Blumkin A K, Edwards K M, Staat M A, et al. The burden of respiratory syncytial virus infection in young children. N Engl J Med. 2009; 360: 588-598. doi:10.1056/NEJMoa0804877
3. Knudson C J, Varga S M. The relationship between respiratory syncytial virus and asthma. Vet Pathol. 2015; 52: 97-106. doi:10.1177/0300985814520639
4. Wu P, Hartert T V. Evidence for a causal relationship between respiratory syncytial virus infection and asthma. Expert Rev Anti Infect Ther. 2011; 9: 731-745. doi: 10.1586/eri.11.92
5. Johnson K M, Bloom H H, Mufson M A, Chanock R M. Natural reinfection of adults by respiratory syncytial virus. Possible relation to mild upper respiratory disease. N Engl J Med. 1962; 267: 68-72. doi:10.1056/NEJM196207122670204
6. Falsey A R, Singh H K, Walsh E E. Serum antibody decay in adults following natural respiratory syncytial virus infection. J Med Virol. 2006; 78: 1493-1497. doi:10.1002/jmv.20724
7. Walsh E E, Falsey A R. Respiratory syncytial virus infection in adult populations. Infect Disord Drug Targets. 2012; 12: 98-102.
8. Schweon S J. Respiratory syncytial virus: More than a pediatric infection. Nursing (Lond). 2015; 45: 64-65. doi:10.1097/01.NURSE.0000463675.37089.95
9. Collins P L, Fearns R, Graham B S. Respiratory syncytial virus: virology, reverse genetics, and pathogenesis of disease. Curr Top Microbiol Immunol. 2013; 372: 3-38. doi:10.1007/978-3-642-38919-1_1
10. Palese P, Zheng H, Engelhardt O G, Pleschka S, García-Sastre A. Negative-strand RNA viruses: genetic engineering and applications. Proc Natl Acad Sci USA. 1996; 93: 11354-11358.
11. Edwards K M, Zhu Y, Griffin M R, Weinberg G A, Hall C B, Szilagyi P G, et al. Burden of human metapneumovirus infection in young children. N Engl J Med. 2013; 368: 633-643. doi:10.1056/NEJMoa1204630
12. Modjarrad K, Giersing B, Kaslow D C, Smith P G, Moorthy V S, WHO RSV Vaccine Consultation Expert Group. WHO consultation on Respiratory Syncytial Virus Vaccine Development Report from a World Health Organization Meeting held on 23-24 Mar. 2015. Vaccine. 2015; doi:10.1016/j.vaccine.2015.05.093
13. Fulginiti V A, Eller J J, Sieber O F, Joyner J W, Minamitani M, Meiklejohn G. Respiratory virus immunization. I. A field trial of two inactivated respiratory virus vaccines; an aqueous trivalent parainfluenza virus vaccine and an alum-precipitated respiratory syncytial virus vaccine. Am J Epidemiol. 1969; 89: 435-448.
14. Kapikian A Z, Mitchell R H, Chanock R M, Shvedoff R A, Stewart C E. An epidemiologic study of altered clinical reactivity to respiratory syncytial (RS) virus infection in children previously vaccinated with an inactivated RS virus vaccine. Am J Epidemiol. 1969; 89: 405-421.
15. Kim H W, Canchola J G, Brandt C D, Pyles G, Chanock R M, Jensen K, et al. Respiratory syncytial virus disease in infants despite prior administration of antigenic inactivated vaccine. Am J Epidemiol. 1969; 89: 422-434.
16. Chin J, Magoffin R L, Shearer L A, Schieble J H, Lennette E H. Field evaluation of a respiratory syncytial virus vaccine and a trivalent parainfluenza virus vaccine in a pediatric population. Am J Epidemiol. 1969; 89: 449-463.
17. Turner T L, Kopp B T, Paul G, Landgrave L C, Hayes D, Thompson R. Respiratory syncytial virus: current and emerging treatment options. Clin Outcomes Res CEOR. 2014; 6: 217-225. doi:10.2147/CEOR.S60710
18. Melero J A, Mas V. The Pneumovirinae fusion (F) protein: A common target for vaccines and antivirals. Virus Res. 2015; doi:10.1016/j.virusres.2015.02.024
19. Graham B S, Modjarrad K, McLellan J S. Novel antigens for RSV vaccines. Curr Opin Immunol. 2015; 35: 30-38. doi:10.1016/j.coi.2015.04.005
20. Dormitzer P R, Grandi G, Rappuoli R. Structural vaccinology starts to deliver. Nat Rev Microbiol. 2012; 10: 807-813. doi:10.1038/nrmicro2893
21. McLellan J S, Ray W C, Peeples M E. Structure and function of respiratory syncytial virus surface glycoproteins. Curr Top Microbiol Immunol. 2013; 372: 83-104. doi:10.1007/978-3-642-38919-1_4
22. González-Reyes L, Ruiz-Argüello M B, García-Barreno B, Calder L, López J A, Albar J P, et al. Cleavage of the human respiratory syncytial virus fusion protein at two distinct sites is required for activation of membrane fusion. Proc Natl Acad Sci USA. 2001; 98: 9859-9864. doi:10.1073/pnas.151098198
23. Najjar F El, Schmitt A P, Dutch R E. Paramyxovirus glycoprotein incorporation, assembly and budding: a three way dance for infectious particle production. Viruses. 2014; 6: 3019-3054. doi:10.3390/v6083019
24. Ghildyal R, Ho A, Jans D A. Central role of the respiratory syncytial virus matrix protein in infection. FEMS Microbiol Rev. 2006; 30: 692-705. doi:10.1111/j.1574-6976.2006.00025.x
25. McLellan J S, Chen M, Leung S, Graepel K W, Du X, Yang Y, et al. Structure of RSV fusion glycoprotein trimer bound to a prefusion-specific neutralizing antibody. Science. 2013; 340: 1113-1117. doi:10.1126/science.1234914
26. Magro M, Mas V, Chappell K, Vazquez M, Cano O, Luque D, et al. Neutralizing antibodies against the preactive form of respiratory syncytial virus fusion protein offer unique possibilities for clinical intervention. Proc Natl Acad Sci USA. 2012; 109: 3089-3094. doi:10.1073/pnas.1115941109
27. Corti D, Bianchi S, Vanzetta F, Minola A, Perez L, Agatic G, et al. Cross-neutralization of four paramyxoviruses by a human monoclonal antibody. Nature. 2013; 501: 439-443. doi:10.1038/nature12442
28. Gilman M S A, Moin S M, Mas V, Chen M, Patel N K, Kramer K, et al. Characterization of a Prefusion-Specific Antibody That Recognizes a Quaternary, Cleavage-Dependent Epitope on the RSV Fusion Glycoprotein. PLoS Pathog. 2015; 11: e1005035. doi:10.1371/journal.ppat.1005035

29. Arruvito L, Raiden S, Geffner J. Host response to respiratory syncytial virus infection. Curr Opin Infect Dis. 2015; 28: 259-266. doi:10.1097/QCO.0000000000000159
30. Lambert L, Sagfors A M, Openshaw P J M, Culley F J. Immunity to RSV in Early-Life. Front Immunol. 2014; 5: 466. doi:10.3389/fimmu.2014.00466
31. Christiaansen A F, Knudson C J, Weiss K A, Varga S M. The CD4 T cell response to respiratory syncytial virus infection. Immunol Res. 2014; 59: 109-117. doi:10.1007/s12026-014-8540-1
32. Roman M, Calhoun W J, Hinton K L, Avendaño L F, Simon V, Escobar A M, et al. Respiratory syncytial virus infection in infants is associated with predominant Th-2-like response. Am J Respir Crit Care Med. 1997; 156: 190-195. doi:10.1164/ajrccm.156.1.9611050
33. Legg J P, Hussain I R, Warner J A, Johnston S L, Warner J O. Type 1 and type 2 cytokine imbalance in acute respiratory syncytial virus bronchiolitis. Am J Respir Crit Care Med. 2003; 168: 633-639. doi:10.1164/rccm.200210-11480C
34. Moghaddam A, Olszewska W, Wang B, Tregoning J S, Helson R, Sattentau Q J, et al. A potential molecular mechanism for hypersensitivity caused by formalin-inactivated vaccines. Nat Med. 2006; 12: 905-907. doi: 10.1038/nm1456
35. De Swart R L, Kuiken T, Timmerman H H, van Amerongen G, Van Den Hoogen B G, Vos H W, et al. Immunization of macaques with formalin-inactivated respiratory syncytial virus (RSV) induces interleukin-13-associated hypersensitivity to subsequent RSV infection. J Virol. 2002; 76: 11561-11569.
36. Stoppelenburg A J, de Roock S, Hennus M P, Bont L, Boes M. Elevated Th17 response in infants undergoing respiratory viral infection. Am J Pathol. 2014; 184: 1274-1279. doi:10.1016/j.ajpath.2014.01.033
37. Mukherjee S, Lindell D M, Berlin A A, Morris S B, Shanley T P, Hershenson M B, et al. IL-17-induced pulmonary pathogenesis during respiratory viral infection and exacerbation of allergic disease. Am J Pathol. 2011; 179: 248-258. doi:10.1016/j.ajpath.2011.03.003
38. McLellan J S, Chen M, Joyce M G, Sastry M, Stewart-Jones G B E, Yang Y, et al. Structure-based design of a fusion glycoprotein vaccine for respiratory syncytial virus. Science. 2013; 342: 592-598. doi:10.1126/science.1243283
39. Liljeroos L, Krzyzaniak M A, Helenius A, Butcher S J. Architecture of respiratory syncytial virus revealed by electron cryotomography. Proc Natl Acad Sci USA. 2013; 110: 11133-11138. doi:10.1073/pnas.1309070110
40. Prince G A, Curtis S J, Yim K C, Porter D D. Vaccine-enhanced respiratory syncytial virus disease in cotton rats following immunization with Lot 100 or a newly prepared reference vaccine. J Gen Virol. 2001; 82: 2881-2888.
41. Graham B S, Perkins M D, Wright P F, Karzon D T. Primary respiratory syncytial virus infection in mice. J Med Virol. 1988; 26: 153-162.
42. McGinnes Cullen L, Schmidt M R, Kenward S A, Woodland R T, Morrison T G. Murine immune responses to virus-like particle-associated pre- and postfusion forms of the respiratory syncytial virus f protein. J Virol. 2015; 89: 6835-6847. doi:10.1128/JVI.00384-15
43. Liang B, Sunnan S, Amaro-Carambot E, Kabatova B, Mackow N, Lingemann M, et al. Enhanced Neutralizing Antibody Response Induced by Respiratory Syncytial Virus Pre-fusion F Protein Expressed by a Vaccine Candidate. J Virol. 2015; doi:10.1128/JVI.01373-15
44. Schickli J H, Whitacre D C, Tang R S, Kaur J, Lawlor H, Peters C J, et al. Palivizumab epitope-displaying virus-like particles protect rodents from RSV challenge. J Clin Invest. 2015; 125: 1637-1647. doi:10.1172/JCI78450
45. Durbin J E, Johnson T R, Durbin R K, Mertz S E, Morotti R A, Peebles R S, et al. The role of IFN in respiratory syncytial virus pathogenesis. J Immunol Baltim Md 1950. 2002; 168: 2944-2952.
46. Sheeran P, Jafri H, Carubelli C, Saavedra J, Johnson C, Krisher K, et al. Elevated cytokine concentrations in the nasopharyngeal and tracheal secretions of children with respiratory syncytial virus disease. Pediatr Infect Dis J. 1999; 18: 115-122.
47. Rutigliano J A, Graham B S. Prolonged production of TNF-alpha exacerbates illness during respiratory syncytial virus infection. J Immunol Baltim Md 1950. 2004; 173: 3408-3417.
48. Miller A L, Bowlin T L, Lukacs N W. Respiratory syncytial virus-induced chemokine production: linking viral replication to chemokine production in vitro and in vivo. J Infect Dis. 2004; 189: 1419-1430. doi:10.1086/382958
49. McNamara P S, Flanagan B F, Hart C A, Smyth R L. Production of chemokines in the lungs of infants with severe respiratory syncytial virus bronchiolitis. J Infect Dis. 2005; 191: 1225-1232. doi:10.1086/428855
50. Henry R L, Hodges I G, Milner A D, Stokes G M. Respiratory problems 2 years after acute bronchiolitis in infancy. Arch Dis Child. 1983; 58: 713-716.
51. Wright P F, Shinozaki T, Fleet W, Sell S H, Thompson J, Karzon D T. Evaluation of a live, attenuated respiratory syncytial virus vaccine in infants. J Pediatr. 1976; 88: 931-936.
52. Broadbent L, Groves H, Shields M D, Power U F. Respiratory syncytial virus, an ongoing medical dilemma: an expert commentary on respiratory syncytial virus prophylactic and therapeutic pharmaceuticals currently in clinical trials. Influenza Other Respir Viruses. 2015; 9: 169-178. doi:10.1111/irv.12313
53. Belshe R B, Van Voris L P, Mufson M A. Parenteral administration of live respiratory syncytial virus vaccine: results of a field trial. J Infect Dis. 1982; 145: 311-319.
54. Le Nouën C, Brock L G, Luongo C, McCarty T, Yang L, Mehedi M, et al. Attenuation of human respiratory syncytial virus by genome-scale codon-pair deoptimization. Proc Natl Acad Sci USA. 2014; 111: 13169-13174. doi:10.1073/pnas.1411290111
55. Whitehead S S, Bukreyev A, Teng M N, Firestone C Y, St Claire M, Elkins W R, et al. Recombinant respiratory syncytial virus bearing a deletion of either the NS2 or SH gene is attenuated in chimpanzees. J Virol. 1999; 73: 3438-3442.
56. Glenn G M, Fries L F, Thomas D N, Smith G, Kpamegan E, Lu H, et al. A randomized, blinded, controlled, dose-ranging study of a respiratory syncytial virus recombinant fusion (F) nanoparticle vaccine in healthy women of childbearing age. J Infect Dis. 2015; doi:10.1093/infdis/jiv406
57. Galarza J M, Latham T, Cupo A. Virus-like particle vaccine conferred complete protection against a lethal influenza virus challenge. Viral Immunol. 2005; 18: 365-372. doi:10.1089/vim.2005.18.365
58. Latham T, Galarza J M. Formation of wild-type and chimeric influenza virus-like particles following simultaneous expression of only four structural proteins. J Virol. 2001; 75: 6154-6165. doi:10.1128/JVI.75.13.6154-6165.2001

59. Matassov D, Cupo A, Galarza J M. A novel intranasal virus-like particle (VLP) vaccine designed to protect against the pandemic 1918 influenza A virus (H1N1). Viral Immunol. 2007; 20: 441-452. doi:10.1089/vim.2007.0027
60. Zhao Q, Li S, Yu H, Xia N, Modis Y. Virus-like particle-based human vaccines: quality assessment based on structural and functional properties. Trends Biotechnol. 2013; 31: 654-663. doi:10.1016/j.tibtech.2013.09.002
61. Luongo C, Winter C C, Collins P L, Buchholz U J. Increased genetic and phenotypic stability of a promising live-attenuated respiratory syncytial virus vaccine candidate by reverse genetics. J Virol. 2012; 86: 10792-10804. doi:10.1128/JVI.01227-12
62. Swanson K A, Settembre E C, Shaw C A, Dey A K, Rappuoli R, Mandl C W, et al. Structural basis for immunization with postfusion respiratory syncytial virus fusion F glycoprotein (RSV F) to elicit high neutralizing antibody titers. Proc Natl Acad Sci USA. 2011; 108: 9619-9624. doi:10.1073/pnas.1106536108
63. Raghunandan R, Lu H, Zhou B, Xabier M G, Massare M J, Flyer D C, et al. An insect cell derived respiratory syncytial virus (RSV) F nanoparticle vaccine induces antigenic site II antibodies and protects against RSV challenge in cotton rats by active and passive immunization. Vaccine. 2014; 32: 6485-6492. doi:10.1016/j.vaccine.2014.09.030
64. Rigter A, Widjaja I, Versantvoort H, Coenjaerts F E J, van Roosmalen M, Leenhouts K, et al. A protective and safe intranasal RSV vaccine based on a recombinant prefusion-like form of the F protein bound to bacterium-like particles. PLoS One. 2013; 8: e71072. doi:10.1371/journal.pone.0071072
65. Bagnaud-Baule A, Reynard O, Perret M, Berland J-L, Maache M, Peyrefitte C, et al. The human metapneumovirus matrix protein stimulates the inflammatory immune response in vitro. PLoS One. 2011; 6: e17818. doi:10.1371/journal.pone.0017818
66. Aerts L, Rhéaume C, Carbonneau J, Lavigne S, Couture C, Hamelin M-È, et al. Adjuvant effect of the human metapneumovirus (HMPV) matrix protein in HMPV subunit vaccines. J Gen Virol. 2015; 96: 767-774. doi:10.1099/vir.0.000031
67. Fox C B, Haensler J. An update on safety and immunogenicity of vaccines containing emulsion-based adjuvants. Expert Rev Vaccines. 2013; 12: 747-758. doi:10.1586/14760584.2013.811188
68. O'Hagan D T, Ott G S, Nest G V, Rappuoli R, Giudice G D. The history of MF59(®) adjuvant: a phoenix that arose from the ashes. Expert Rev Vaccines. 2013;12: 13-30. doi:10.1586/erv.12.140
69. Knudson C J, Hartwig S M, Meyerholz D K, Varga S M. RSV vaccine-enhanced disease is orchestrated by the combined actions of distinct CD4 T cell subsets. PLoS Pathog. 2015; 11: e1004757. doi:10.1371/journal.ppat.1004757
70. Coffman R L, Sher A, Seder R A. Vaccine adjuvants: putting innate immunity to work. Immunity. 2010; 33: 492-503. doi:10.1016/j.immuni.2010.10.002
71. Lindblad E B. Aluminium compounds for use in vaccines. Immunol Cell Biol. 2004; 82: 497-505. doi:10.1111/j.0818-9641.2004.01286.x
72. Loebbermann J, Schnoeller C, Thornton H, Durant L, Sweeney N P, Schuijs M, et al. IL-10 regulates viral lung immunopathology during acute respiratory syncytial virus infection in mice. PLoS One. 2012; 7: e32371. doi:10.1371/journal.pone.0032371
73. Widjaja I, Rigter A, Jacobino S, van Kuppeveld F J M, Leenhouts K, Palomo C, et al. Recombinant Soluble Respiratory Syncytial Virus F Protein That Lacks Heptad Repeat B, Contains a GCN4 Trimerization Motif and Is Not Cleaved Displays Prefusion-Like Characteristics. PLoS One. 2015; 10: e0130829. doi:10.1371/journal.pone.0130829
74. Ueba O. Respiratory syncytial virus. I. Concentration and purification of the infectious virus. Acta Med Okayama. 1978; 32: 265-272.
75. Bliss CI. THE METHOD OF PROBITS. Science. 1934; 79: 38-39. doi:10.1126/science.79.2037.38
76. Moreno P R, Palacios I F, Leon M N, Rhodes J. Fuster V, Fallon J T. Histopathologic comparison of human coronary in-stent and post-balloon angioplasty restenotic tissue. Am J Cardiol. 1999; 84: 462-466, A9.

What is claimed is:

1. A virus-like particle (VLP) comprising
at least one human metapneumovirus (hMPV) matrix (M) protein; and
a prefusion surface respiratory syncytial virus (RSV) F protein and a postfusion RSV F protein, wherein transmembrane and cytoplasmic domains of the prefusion and postfusion RSV F proteins are replaced with analogous amino acid sequences from an hMPV F protein, wherein the prefusion RSV F protein comprises the following substitutions relative to SEQ ID NO: 1: A102C, I148C, S155C and S290C, and wherein the prefusion RSV F protein is modified at both of furin cleavage site RARR at residues 106 to 109 of SEQ ID NO: 1 to KAHQ of SEQ ID NO: 5 and furin cleavage site RKRR at residues 133 to 136 of SEQ ID NO: 1 to KKQH of SEQ ID NO: 7.

2. The VLP of claim 1, further comprising one or more G protein and/or one or more SH protein.

3. The VLP of claim 1, wherein the hMPV matrix protein and the RSV F proteins are codon optimized.

4. The VLP of claim 1, wherein at least one RSV F protein comprises one or more of the following substitutions: numbered relative to SEQ ID NO:1: E30C, F32C, N105C, G145C, L467C, Y486C, V469C.

5. The VLP of claim 1, where the RSV F proteins are linked to the hMPV M protein through a linker peptide.

6. A DNA construct comprising sequences encoding pneumovirus viral proteins used to assemble the VLP of claim 1, the DNA construct comprising sequences encoding the hMPV and RSV proteins.

7. A method of producing a VLP, the method comprising introducing into a host cell one or more DNA constructs according to claim 6 under conditions such that the cell produces the VLP.

8. The method of claim 7, wherein the host cell is a eukaryotic cell selected from the group consisting of mammalian, yeast, insect, plant, amphibian and avian cells.

9. The method of claim 7, wherein the cells are cultured at temperatures ranging from 25° C. to 37° C.

10. A VLP generated by the method of claim 7.

11. An immunogenic composition comprising at least one VLP according to claim 1.

12. The immunogenic composition of claim 11, further comprising an adjuvant.

13. A method of generating an immune response to one or more pneumoviruses in a subject, the method comprising administering to the subject an effective amount of the immunogenic composition according to claim 11.

14. The method of claim 13, wherein the composition is administered mucosally, intradermally, subcutaneously, intramuscularly, or orally.

15. The method of claim 13, wherein the immune response vaccinates the subject against multiple serotypes or clades of one or more pneumoviruses.

16. The method of claim 13, wherein the subject is a human.

* * * * *